United States Patent
Wang et al.

(10) Patent No.: US 11,891,689 B2
(45) Date of Patent: Feb. 6, 2024

(54) LOW-CAPACITANCE NANOPORE SENSORS ON INSULATING SUBSTRATES

(71) Applicant: Arizona Board of Regents on behalf of Arizona State University, Scottsdale, AZ (US)

(72) Inventors: Chao Wang, Chandler, AZ (US); Pengkun Xia, Tempe, AZ (US)

(73) Assignee: Arizona Board of Regents on behalf of Arizona State University, Scottsdale, AZ (US)

( * ) Notice: Subject to any disclaimer, the term of this patent is extended or adjusted under 35 U.S.C. 154(b) by 0 days.

(21) Appl. No.: 17/908,795

(22) PCT Filed: Mar. 3, 2021

(86) PCT No.: PCT/US2021/020585
§ 371 (c)(1),
(2) Date: Sep. 1, 2022

(87) PCT Pub. No.: WO2021/178477
PCT Pub. Date: Sep. 10, 2021

(65) Prior Publication Data
US 2023/0091639 A1    Mar. 23, 2023

Related U.S. Application Data

(60) Provisional application No. 62/984,381, filed on Mar. 3, 2020.

(51) Int. Cl.
*C23C 16/04* (2006.01)
*B01L 3/00* (2006.01)
(Continued)

(52) U.S. Cl.
CPC ...... *C23C 16/042* (2013.01); *B01L 3/502761* (2013.01); *C12Q 1/6869* (2013.01);
(Continued)

(58) Field of Classification Search
CPC .................. H01L 21/0332; H01L 21/0337
See application file for complete search history.

(56) References Cited

U.S. PATENT DOCUMENTS 9,017,937 B1    4/2015   Turner et al.
RE47,067 E     10/2018   Turner et al.
(Continued)

FOREIGN PATENT DOCUMENTS

| CN | 102064088 B | 10/2012 | |
|---|---|---|---|
| WO | WO-2018136497 A1 * | 7/2018 | ....... G01N 33/48721 |
| WO | WO2018136497 A1 | 7/2018 | |

OTHER PUBLICATIONS

Albrecht, "Single-Molecule Analysis with Solid-State Nanopores," Annual Rev. Anal. Chem., 2019, 12(1):371-387.
(Continued)

*Primary Examiner* — Binh X Tran
(74) *Attorney, Agent, or Firm* — Fish & Richardson P.C.

(57) ABSTRACT

Fabricating a nanopore sensor includes depositing a first and second oxide layers on first and second sides of a sapphire substrate. The second oxide layer is patterned to form an etch mask having a mask opening in the second oxide layer. A crystalline orientation dependent wet anisotropic etch is performed on the second side of the sapphire substrate using the etch mask to form a cavity having sloped side walls through the sapphire substrate to yield an exposed portion of the first oxide layer, each of the sloped side walls being a crystalline facet aligned with a respective crystalline plane of the sapphire substrate. A silicon nitride layer is deposited on the first oxide layer. The exposed portion of the first oxide layer in the cavity is removed, thereby defining a silicon nitride membrane in the cavity. An opening is formed through the silicon nitride membrane.

15 Claims, 11 Drawing Sheets

(51) Int. Cl.
- C12Q 1/6869 (2018.01)
- C23C 16/02 (2006.01)
- C23C 16/34 (2006.01)
- G01N 27/04 (2006.01)
- G01N 33/487 (2006.01)

(52) U.S. Cl.
CPC ........ *C23C 16/0227* (2013.01); *C23C 16/345* (2013.01); *G01N 27/04* (2013.01); *G01N 33/48721* (2013.01); *B01L 2200/0647* (2013.01); *B01L 2300/0645* (2013.01); *B01L 2300/16* (2013.01)

(56) References Cited

U.S. PATENT DOCUMENTS

| | | | |
|---|---|---|---|
| 10,488,394 | B2 | 11/2019 | Liu et al. |
| 2002/0053915 | A1 | 5/2002 | Weaver et al. |
| 2002/0115198 | A1 | 8/2002 | Nerenberg et al. |
| 2006/0098927 | A1 | 5/2006 | Schmidt et al. |
| 2007/0172386 | A1 | 7/2007 | Li et al. |
| 2016/0017340 | A1* | 1/2016 | Wu ........................ C12M 35/02 435/375 |

OTHER PUBLICATIONS

An et al., "Ultrafast laser fabrication of submicrometer pores in borosilicate glass," Optics Letters, 2008, 33(10):1153-1155.

Assad et al., "Two color DNA barcode detection in photoluminescence suppressed silicon nitride nanopores," Nano Lett., 2014, 15:745-752.

Bai et al., "Fabrication of sub-20 nm nanopore arrays in membranes with embedded metal electrodes at wafer scales," Nanoscale, 2014, 6:8900-8906.

Balan et al., "Improving signal-to-noise performance for DNA translocation in solid-state nanopores at MHz bandwidths," Nano Lett. 2014, 14(12):7215-7220.

Balan et al., "Suspended Solid-state Membranes on Glass Chips with Sub 1-pF Capacitance for Biomolecule Sensing Applications," Scientific Reports, 2015, 5:17775, 8 pages.

Bentley et al., "Accurate whole human genome sequencing using reversible terminator chemistry," Nature, 2008, 456:53-59.

Branton et al., "The potential and challenges of nanopore sequencing," Nat. Biotechnol., 2008, 26(10):1146-1153.

Chen et al., "Evolution of bottom c-Plane on wet-etched patterned sapphire substrate," ECS J. Solid State Sci. Technol., 2013, 2(9):R169-R171.

Chen et al., "The formation and the plane indices of etched facets of wet etching patterned sapphire substrate," J. Electrochem. Soc., 2012, 159(6):D362-D366.

Chen et al., "The Formation of Smooth Facets on Wet-Etched Patterned Sapphire Substrate," ECS J. Solid State Sci. Technol., 2014, 3(2):R5-R8.

Cheryan et al., "Why are some STEM fields more gender balanced than others?" Psychological Bulletin, 2017, 143(1):1-35.

Clarke et al., "Continuous base identification for single-molecule nanopore DNA sequencing," Nat. Nanotechnol., 2009, 4:265-270.

Crowley et al., "Resolution of the band gap prediction problem for materials design," J. Phys. Chem. Lett., 2016, 7:1198-1203.

Danda et al., "Monolayer WS2 Nanopores for DNA Translocation with Light-Adjustable Sizes," ACS Nano, 2017, 11(2):1937-1945.

Davis, "III-V nitrides for electronic and optoelectronic applications," Proceedings of the IEEE, 1991, 79:702-712.

De Vreede et al., "Wafer-scale fabrication of fused silica chips for low-noise recording of resistive pulses through nanopores," Nanotechnology, 2019, 30(26):265301, 13 pages.

Dekker, "Solid-state nanopores," Nat. Nanotechnol., 2007, 2(4):209-215.

Deng et al., "Fabrication of Inverted-Pyramid Silicon Nanopore Arrays with Three-StepWet Etching," ECS J. Solid State Sci. Technol., 2013, 2:P419-P422.

Diekman et al., "Seeking congruity between goals and roles: A new look at why women opt out of science, technology, engineering, and mathematics careers," Psychological Science, 2010, 21(8):1051-1057.

Dimitrov et al., "Nanopores in solid-state membranes engineered for single molecule detection," Nanotechnology, 2010, 21:065502, 12 pages.

Eid et al., "Real-Time DNA Sequencing from Single Polymerase Molecules," Science, 2009, 323:133-138.

Farimani et al., "DNA base detection using a single-layer MoS2," ACS Nano, 2014, 8(8):7914-7922.

Feng et al., "Identification of single nucleotides in MoS2 nanopores," Nat. Nanotechnol., 2015, 10:1070-1076.

Ferrari et al., "Transimpedance amplifier for high sensitivity current measurements on nanodevices," IEEE J. Solid-State Circuits, 2009, 44:1609-1616.

Fologea et al., "Slowing DNA Translocation in a Solid-State Nanopore," Nano Letters, 2005, 5(9):1734-1737.

genome.gov [online], "The Cost of Sequencing a Human Genome," available on or before Dec. 22, 2017, via Internet Archive: Wayback Machine URL <http://web.archive.org/web/20171222192030/https://www.genome.gov/sequencingcosts/>, retrieved on Dec. 14, 2022, URL <https://www.genome.gov/sequencingcosts/>, 7 pages.

Gilboa et al., "Automated, Ultra-Fast Laser-Drilling of Nanometer Scale Pores and Nanopore Arrays in Aqueous Solutions," Adv. Funct. Mater., 2020, 30(18):1900642, 9 pages.

Gilboa et al., "Optical sensing and analyte manipulation in solid-state nanopores," Analyst, 2015, 140:4733-4747.

Gilboa et al., "Optically-monitored nanopore fabrication using a focused laser beam," Scientific Reports, 2018, 8:9765, 10 pages.

Gilboa et al., "Single-Molecule DNA Methylation Quantification Using Electro-optical Sensing in Solid-State Nanopores," ACS Nano, 2016, 10:8861-8870.

Goldberg et al., "Epigenetics: a landscape takes shape," Cell, 2007, 128:635-638.

Gonzaga-Jauregui et al., "Human genome sequencing in health and disease," Annu. Rev. Med., 2012, 63:35-61 (Author Manuscript).

Goodwin et al., "Coming of age: ten years of next-generation sequencing technologies," Nature Reviews Genetics, 2016, 17:333-351.

Graf et al., "Fabrication and practical applications of molybdenum disulfide nanopores," Nature Protocols, 2019, 14(4):1130-1168.

Hall et al., "Hybrid pore formation by directed insertion of α-haemolysin into solid-state nanopores," Nat. Nanotechnol., 2010, 5:874-877.

He et al., "Controlling DNA Translocation through Gate Modulation of Nanopore Wall Surface Charges," ACS Nano, 2011, 5(7):5509-5518.

Ivanov et al., "DNA Tunneling Detector Embedded in a Nanopore," Nano Lett., Jan. 2011, 11:279-285.

Kasianowicz et al., "Characterization of individual polynucleotide molecules using a membrane channel," Proc. Natl. Acad. Sci. U.S.A., Nov. 1996, 93:13770-13773.

Kwak et al., "Probing the Small-Molecule Inhibition of an Anticancer Therapeutic Protein-Protein Interaction Using a Solid-State Nanopore," Angew. Chem., 2016, 128(19):5807-5811.

Kwok et al., "Nanopore fabrication by controlled dielectric breakdown," PloS One, Mar. 2014, 9(3):e92880, 6 pages.

Laird et al., "The role of DNA methylation in cancer genetics and epigenetics," Annu. Rev. Genet., 1996, 30:441-464.

Laird, "Principles and challenges of genome-wide DNA methylation analysis," Nat. Rev. Genet., Mar. 2010, 11:191-203.

Landan et al., "Epigenetic polymorphism and the stochastic formation of differentially methylated regions in normal and cancerous tissues," Nat. Genet., Nov. 2012, 44(11):1207-1214.

Landau et al., "Locally disordered methylation forms the basis of intratumor methylome variation in chronic lymphocytic leukemia," Cancer Cell, Dec. 2014, 26:813-825.

Lander et al., "Initial sequencing and analysis of the human genome," Nature, Feb. 2001, 409:860-921.

(56) References Cited

OTHER PUBLICATIONS

Laturia et al., "Dielectric properties of hexagonal boron nitride and transition metal dichalcogenides: from monolayer to bulk," NPJ 2D Mater. Appl., Mar. 2018, 2(1):6, 7 pages.
Lee et al., "A low-noise solid-state nanopore platform based on a highly insulating substrate," Scientific Reports, 2014, 4:7448, 7 pages.
Levis et al., "The Use of Quartz Patch Pipettes for Low Noise Single Channel Recording," Biophysical Journal, Oct. 1993, 65:1666-1677.
Li et al., "DNA molecules and configurations in a solid-state nanopore microscope," Nature Materials, Sep. 2003, 2:611-615.
Li et al., "Single Protein Molecule Detection by Glass Nanopores," ACS Nano, 2013, 7(5):4129-4134.
Liang et al., "Noise in nanopore sensors: Sources, models, reduction, and benchmarking," Nanotechnol. Precis. Eng., 2020, 3:9-17.
Lindsay, "The promises and challenges of solid-state sequencing," Nature Nanotechnology, Feb. 2016, 11:109-111.
Margulies et al., "Genome sequencing in microfabricated high-density picolitre reactors," Nature, Sep. 2005, 437:376-380.
McNally et al., "Optical recognition of converted DNA nucleotides for single-molecule DNA sequencing using nanopore arrays," Nano Lett., 2010, 10:2237-2244.
Meller et al., "Rapid nanopore discrimination between single polynucleotide molecules," Proc. Natl. Acad. Sci. U.S.A., Feb. 2000, 97(3):1079-1084.
Meller et al., "Voltage-driven DNA translocations through a nanopore," Phys. Rev. Lett., Apr. 2001, 86(15):3435-3438.
Metzker, "Sequencing technologies—the next generation," Nat. Rev. Genet., Jan. 2010, 11:31-46.
Nagai et al., "Anisotropic diamond etching through thermochemical reaction between Ni and diamond in high-temperature water vapour," Scientific Reports, Apr. 2018, 8:6687, 8 pages.
nsf.gov [online], "Women, Minorities, and Persons with Disabilities in Science and Engineering," Jan. 2017, retrieved on Oct. 18, 2022, retrieved from URL <https://www.nsf.gov/statistics/2017/nsf17310/>, 1 page.
O'Donnell et al., "Error analysis of idealized nanopore sequencing," Electrophoresis, 2013, 34:2137-2144.
Ohayon et al. Simulation of single-protein nanopore sensing shows feasibility for whole-proteome identification, PLoS Comp. Biol., 2019, 15:e1007067, 21 pages.
Ohshiro et al., "Single-molecule electrical random resequencing of DNA and RNA," Scientific Reports, Jul. 2012, 2:501, 7 pages.
Okazaki et al., "Wet Etching of Amorphous TiO2 Thin Films Using H3PO4—H2O2 Aqueous Solution," Jpn. J. Appl. Phys., 2013, 52:098002, 4 pages.
Pang et al., "Fixed-Gap Tunnel Junction for Reading DNA Nucleotides," ACS Nano, 2014, 8(12):11994-12003.
Park et al., "Noise and sensitivity characteristics of solid-state nanopores with a boron nitride 2-D membrane on a pyrex substrate," Nanoscale, 2016, 8(10):5755-5763.
Pérez-Mitta et al., "Molecular Design of Solid-State Nanopores: Fundamental Concepts and Applications," Adv. Mater., 2019, 31(37):1901483, 46 pages.
Pitchford et al., "Synchronized optical and electronic detection of biomolecules using a low noise nanopore platform," ACS Nano, 2015, 9(2):1740-1748.
Raillon et al., "Fast and automatic processing of multi-level events in nanopore translocation experiments," Nanoscale, 2012, 4(16):4916-4924.
Rangsten et al., "Etch rates of crystallographic planes in Z-cut quartz-experiments and simulation," J. Micromech. Microeng., 1998, 8:1-6.
Rodriguez-Manzo et al., "DNA Translocation in Nanometer Thick Silicon Nanopores," ACS Nano, 2015, 9(6):6555-6564.
Rosenstein et al., "Integrated nanopore sensing platform with sub-microsecond temporal resolution," Nat. Methods, 2012, 9(5):487-492, Author Manuscript.
Schneider et al., "DNA translocation through graphene nanopores," Nano Lett., 2010, 10:3163-3167.
Schübeler, "Function and information content of DNA methylation," Nature, Jan. 2015, 517:321-326.
Serandour et al., "Dynamic hydroxymethylation of deoxyribonucleic acid marks differentiation-associated enhancers," Nucleic Acids Res., 2012, 40(17):8255-8265.
Shapovalov et al., "Gating transitions in bacterial ion channels measured at 3 µs resolution," J. Gen. Physiol., Aug. 2004, 124:151-161.
Shekar et al., "Measurement of DNA Translocation Dynamics in a Solid-State Nanopore at 100 ns Temporal Resolution," Nano Lett., 2016, 16:4483-4489.
Singer et al., "Electronic barcoding of a viral gene at the single-molecule level," Nano Lett., 2012, 12:1722-1728.
Siwy et al., "Engineered voltage-responsive nanopores," Chem. Soc. Rev., 2010, 39:1115-1132.
Siwy et al., "Fabrication of a Synthetic Nanopore Ion Pump," Phys. Rev. Lett., Nov. 2002, 89(19):198103, 4 pages.
Smeets et al., "Noise in solid-state nanopores," Proc. Natl. Acad. Sci. U.S.A., Jan. 2008, 105(2):417-421.
Smith et al., "DNA methylation: roles in mammalian development," Nat. Rev. Genet., Mar. 2013, 14:204-220.
Soni et al., "Synchronous optical and electrical detection of biomolecules traversing through solid-state nanopores," Rev. Sci. Instrum., 2010, 81:014301, 8 pages.
Squires et al., "Genomic pathogen typing using solid-state nanopores," PloS One, Nov. 2015, 10:e0142944, 16 pages.
Steinbock et al., "DNA translocation through low-noise glass nanopores," ACS Nano, 2013, 7(12):11255-11262.
Stocker et al., "Crystallographic wet chemical etching of GaN," Appl. Phys. Lett., Nov. 1998, 73(18):2654-2656.
Stoddart et al., "Single-nucleotide discrimination in immobilized DNA oligonucleotides with a biological nanopore," Proc. Natl. Acad. Sci. U.S.A., May 2009, 106(19):7702-7707.
Sundaram et al., "Wet etching studies of silicon nitride thin films deposited by electron cyclotron resonance (ECR) plasma enhanced chemical vapor deposition," Microelectron. Eng., 2003, 70:109-114.
Tabard-Cossa et al., "Noise analysis and reduction in solid-state nanopores," Nanotechnology, 2007, 18(30):305505, 7 pages.
Uram et al., "Noise and Bandwidth of Current Recordings from Submicrometer Pores and Nanopores," ACS Nano, 2008, 2(5):857-872.
Venta et al., "Differentiation of short, single-stranded DNA homopolymers in solid-state nanopores," ACS Nano, 2013, 7(5):4629-4636.
Wang et al., "Single-Molecule Discrimination of Labeled DNAs and Polypeptides Using Photoluminescent-Free TiO2 Nanopores," ACS Nano, 2018, 12:11648-11656.
Wanunu et al., "DNA Translocation Governed by Interactions with Solid-State Nanopores," Biophys. J., Nov. 2008, 95(10):4716-4725.
Wanunu et al., "Rapid electronic detection of probe-specific microRNAs using thin nanopore sensors," Nat. Nanotechnol., 2010, 5:807-814.
Wen et al., "Generalized Noise Study of Solid-State Nanopores at Low Frequencies," ACS Sens., 2017, 2(2):300-307.
Xia et al., "Sapphire-supported nanopores for low-noise DNA sensing," Biosens Bioelectron., Feb. 2021, 174:112829, 8 pages.
Xing et al., "Characterization of anisotropic wet etching of single-crystal sapphire," Sens. Actuators A, 2019, 303:111667, 9 pages.
Yamazaki et al., "Photothermally Assisted Thinning of Silicon Nitride Membranes for Ultrathin Asymmetric Nanopores," ACS Nano, 2018, 12(12):12472-12481.
Yusko et al., "Real-time shape approximation and fingerprinting of single proteins using a nanopore," Nature Nanotechnology, Apr. 2017, 12(4):360-367.
Zahid et al., "Quantifying mammalian genomic DNA hydroxymethylcytosine content using solid-state nanopores," Scientific Reports, 2016, 6:29565, 6 pages.
Zhuang et al., "Wet etching of GaN, AlN, and SiC: a review," Materials Science and Engineering R, 2005, 48:1-46.
International Search Report and Written Opinion in International Appln. No. PCT/US2021/020585, dated May 24, 2021, 7 pages.

\* cited by examiner

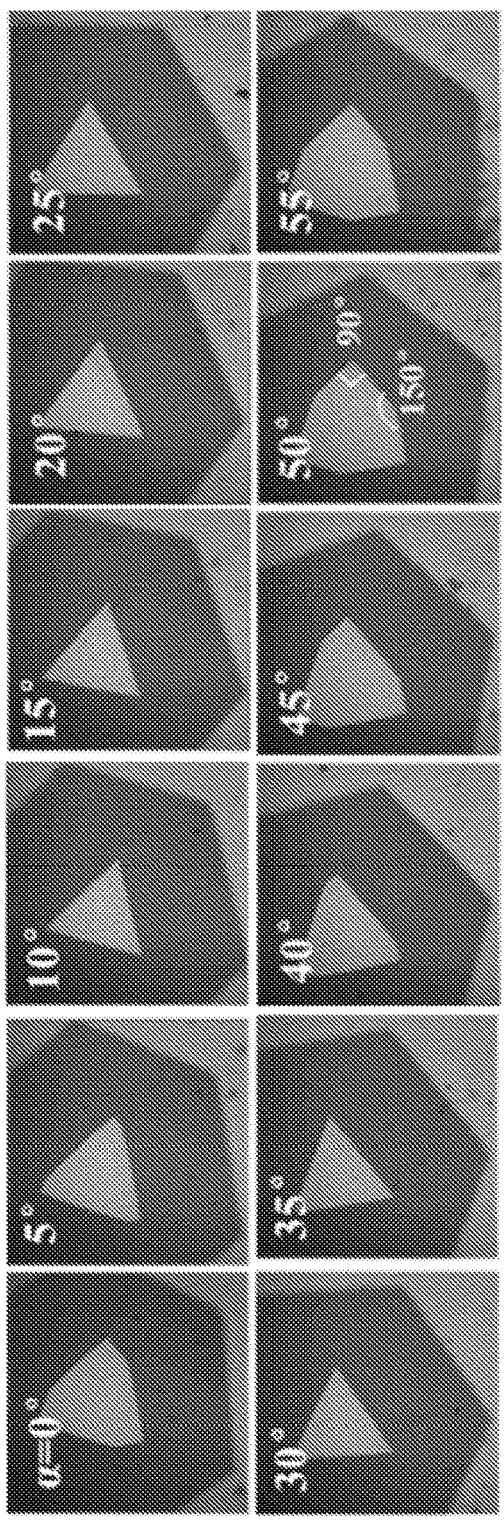
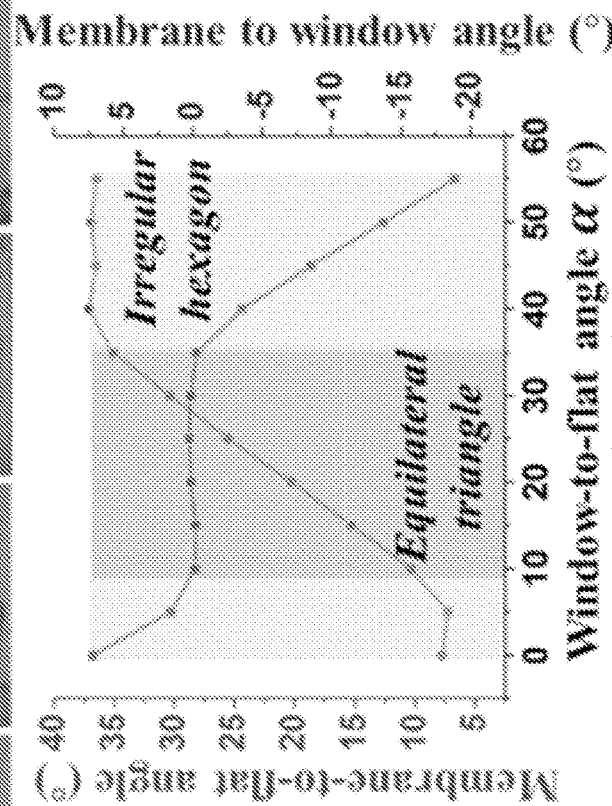
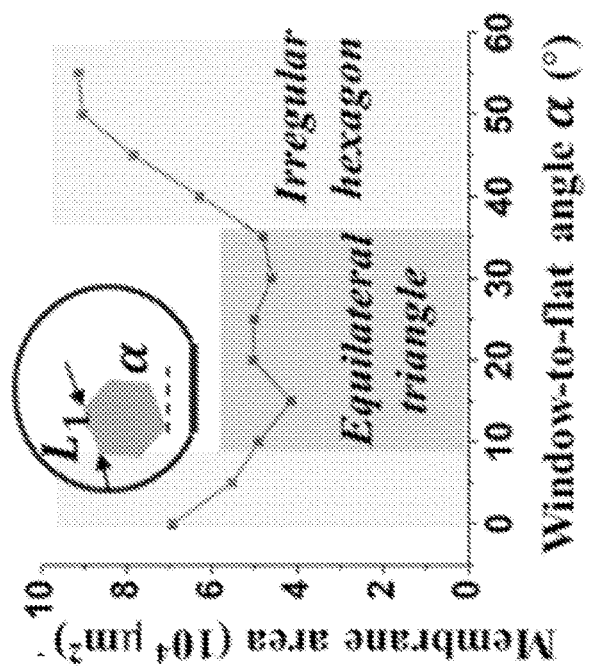
FIG. 9A
FIG. 9B
FIG. 9C

LOW-CAPACITANCE NANOPORE SENSORS ON INSULATING SUBSTRATES

CROSS-REFERENCE TO RELATED APPLICATIONS

This application is a National Stage Application of International Application No. PCT/US2021/020585, filed Mar. 3, 2021, which claims the benefit of U.S. Patent Application No. 62/984,381 entitled "LOW-CAPACITANCE NANOPORE SENSORS ON INSULATING SUBSTRATES" and filed on Mar. 3, 2020. Both of these applications are incorporated herein by reference in their entirety.

TECHNICAL FIELD

This invention relates to low-capacitance nanopore sensors on insulating substrates fabricated with circular or polygonal etching windows.

BACKGROUND

Nanopore-based electronic DNA sequencing is promising in clinical use and personal medical care for its portability, high speed, low cost, and long DNA read length. However, despite improvements in the nanopore structure design and data analysis algorithms, it remains extremely difficult to accurately interpret the DNA sequence from the electrical signals. One challenge is associated with an insufficient signal-to-noise ratio (SNR) that limits the signal reading speed and resolving power.

SUMMARY

Sapphire-supported (SaS) nanopore sensors for high-speed, sensitive, and low-noise DNA detection using thin membranes on insulating crystal wafers (e.g., sapphire) are described. Substrate insulation reduces conductance-based capacitance and the feasibility of controlling membrane dimension down to <10 μm allows reduced chip capacitance even for ultrathin (~1 nm) membrane materials (e.g., low-dimensional materials). Thus, nanopore chip capacitance can be reduced by orders of magnitude compared with that of a typical silicon (Si) chip, thus reducing the background high-frequency electrical noise and improving high-bandwidth sensing. The low device capacitance is also favorable for fast circuit response. Further, the membrane creation in sapphire is batch-processing compatible, and will allow high-throughput, low-cost production for device implementation. Additionally, the single-crystalline and insulating (bandgap ~10 eV) nature of the sapphire can suppress leakage current and photoluminescence background for high DNA signal integrity, feasible for both low-noise electrical and optical sensing. A hexagonal window design can be used to fabricate membranes shaped as irregular hexagons or equilateral triangles.

A method for reproducibly creating SaS nanopores triangular membranes with <25 μm dimensions on 2-inch sapphire wafers is also described. Completely eliminating the substrate conductivity-induced stray capacitance, these SaS nanopores produced two-order-of-magnitude smaller device capacitance (10 pF) compared to a measured SiS nanopore (~1.3 nF), despite having a 100 times larger membrane area. Accordingly, the SaS nanopores generated ~2.6 times smaller RMS ionic current noise than the SiS nanopore at 100 kHz bandwidth, which resulted in high-fidelity DNA sensing with two times higher SNR despite a larger nanopore size and thicker SiN membrane. The SaS nanopore sensor can also be used to interrogate a variety of other biomolecules at single-molecule level, such as RNA, protein, and extracellular vesicles, and their molecular interactions at improved speed and accuracy.

Embodiment 1 is a method of fabricating a nanopore sensor, the method comprising depositing a first oxide layer on a first side of a sapphire substrate and a second oxide layer on a second side of the sapphire substrate opposite the first side; patterning the second oxide layer to form an etch mask having a mask opening in the second oxide layer; performing a crystalline orientation dependent wet anisotropic etch on the second side of the sapphire substrate using the etch mask to form a cavity having sloped side walls through the sapphire substrate to yield an exposed portion of the first oxide layer, each of the sloped side walls being a crystalline facet aligned with a respective crystalline plane of the sapphire substrate; depositing a silicon nitride layer on the first oxide layer; removing the exposed portion of the first oxide layer in the cavity, thereby defining a silicon nitride membrane in the cavity; and forming an opening through the silicon nitride membrane, wherein the opening is a nanopore with a diameter in a range of 1 nm to 20 nm.

Embodiment 2 is the method of embodiment 1, wherein the mask opening is in the shape of a circle.

Embodiment 3 is the method of any one of embodiments 1 through 2, wherein the silicon nitride membrane is polygonal and has three-fold symmetry.

Embodiment 4 is the method of any one of embodiments 1 through 3, wherein the polygonal silicon nitride membrane has 6 edges.

Embodiment 5 is the method of any one of embodiments 1 through 4, wherein the mask opening is in the shape of a polygon, Embodiment 6 is the method of any one of embodiments 1 through 5, wherein the polygon is an equilateral triangle, and an edge of the equilateral triangle is aligned at an offset angle $\alpha$ from a crystalline plane of the sapphire substrate, where $0°<\alpha<60°$.

Embodiment 7 is the method of any one of embodiments 1 through 6, wherein the silicon nitride membrane is in the shape of an equilateral triangle when $0°<\alpha<20°$ and $40°<\alpha<60°$.

Embodiment 8 is the method of any one of embodiments 1 through 7, wherein the silicon nitride membrane is in the shape of a nonagon when $20°<\alpha<40°$.

Embodiment 9 is the method of any one of embodiments 1 through 8, wherein the polygon is a hexagon.

Embodiment 10 is the method of any one of embodiments 1 through 9, wherein an edge of the hexagon is aligned at an offset angle $\alpha$ from a crystalline plane of the sapphire substrate, where $5°<\alpha<55°$.

Embodiment 11 is the method of any one of embodiments 1 through 10, wherein the silicon nitride membrane is in the shape of an equilateral triangle when $10°<\alpha<35°$.

Embodiment 12 is the method of any one of embodiments 1 through 11, wherein an area of the silicon nitride membrane is substantially constant when $10°<\alpha<35°$.

Embodiment 13 is the method of any one of embodiments 1 through 2, wherein sides of the silicon nitride membrane are parallel to sides of the hexagon when $10°<\alpha<35°$.

Embodiment 14 is the method of any one of embodiments 1 through 13, wherein the silicon nitride membrane is in the shape of an irregular hexagon when $\alpha<10°$ or $\alpha>35°$.

Embodiment 15 is the method of any one of embodiments 1 through 14, wherein sides of the irregular hexagon are oriented along particular crystal orientations of the sapphire substrate.

Embodiment 16 is the method of any one of embodiments 1 through 15, wherein interior angles of the irregular hexagon are between about 90° and 150°.

Embodiment 17 is the method of any one of embodiments 1 through 16, wherein a duration of the etch is in a range of minutes to hours.

Embodiment 18 is the method of any one of embodiments 1 through 17, wherein the etch is conducted at a temperature in a range between 150° C. and 450° C.

Embodiment 19 is the method of any one of embodiments 1 through 18, wherein a dimension of a surface of the sapphire substrate is in a range between about 1 mm and about 20 cm and a thickness of the sapphire substrate is in a range between about 0.1 mm and about 1 mm.

Embodiment 20 is a nanopore sensor comprising a sapphire substrate defining a first opening and second opening, wherein the first opening and the second opening are superimposed; and a silicon nitride membrane extending across the second opening and defining a nanopore therethrough, wherein the membrane is in the shape of a polygon.

Embodiment 21 is the method of embodiment 20, wherein the first opening is in the shape of a circle.

Embodiment 22 is the method of any one of embodiments 20 through 21, wherein the silicon nitride membrane is polygonal and has three-fold or six-fold symmetry.

Embodiment 23 is the method of any one of embodiments 20 through 22, wherein the polygonal silicon nitride membrane has 6 edges.

Embodiment 24 is the method of any one of embodiments 20 through 23, wherein the mask opening is in the shape of a polygon, Embodiment 25 is the method of any one of embodiments 20 through 24, wherein the polygon is an equilateral triangle, and an edge of the equilateral triangle is aligned at an offset angle $\alpha$ from a crystalline plane of the sapphire substrate, where $0°<\alpha<60°$.

Embodiment 26 is the method of any one of embodiments 20 through 25, wherein the silicon nitride membrane is in the shape of an equilateral triangle when $0°<\alpha<20°$ or $40°<\alpha<60°$.

Embodiment 27 is the method of any one of embodiments 20 through 26, wherein the silicon nitride membrane is in the shape of a nonagon when $20°<\alpha<40°$.

Embodiment 28 is the method of any one of embodiments 20 through 27, wherein the polygon is a hexagon.

Embodiment 29 is the method of any one of embodiments 20 through 28, wherein an edge of the hexagon is aligned at an offset angle $\alpha$ from a crystalline plane of the sapphire substrate, wherein $5°<\alpha<55°$.

Embodiment 30 is the method of any one of embodiments 20 through 29, wherein the silicon nitride membrane is in the shape of an equilateral triangle when $10°<\alpha<35°$.

Embodiment 31 is the method of any one of embodiments 20 through 30, wherein sides of the silicon nitride membrane are parallel to sides of the hexagon when $10°<\alpha<35°$.

Embodiment 32 is the method of any one of embodiments 20 through 31, wherein the silicon nitride membrane is in the shape of an irregular hexagon when $\alpha<10°$ or $\alpha>35°$.

Embodiment 33 is the method of any one of embodiments 20 through 32, wherein sides of the irregular hexagon are oriented along particular crystal orientations of the sapphire substrate.

Embodiment 34 is the method of any one of embodiments 20 through 33, wherein interior angles of the irregular hexagon are between about 90° and 150°.

The details of one or more embodiments of the subject matter of this disclosure are set forth in the accompanying drawings and the description. Other features, aspects, and advantages of the subject matter will become apparent from the description, the drawings, and the claims.

BRIEF DESCRIPTION OF DRAWINGS

FIG. 9A shows optical images of Sift/sapphire membranes formed with hexagonal masks with angle $\alpha$ in 5° increments from 0° to 55°.

FIG. 9B shows membrane area dependence on the window-to-flat alignment angle $\alpha$.

FIG. 9C shows the measured membrane-to-flat angle and membrane-to-window angle as a changes.

DETAILED DESCRIPTION

Embodiments of die present invention provide a method for forming a low-noise nanopore sensor in a thin membrane suspended on an insulating substrate, for example, a sapphire substrate. In some embodiments, the manufacturing method of such nanopore devices on sapphire includes using controlled anisotropic wet etching, in which the etch rates are dependent on the crystal orientation of sapphire and hence can precisely control the membrane size by the design of an etching mask. Insulating materials, such as silicon oxide, silicon nitride, etc., have been used as the membrane layer in which the nanopore is formed. Wet etching of sapphire substrates can have a high etching rate of 0.1 μm to 1 μm per minute, allowing etching through the thickness of the sapphire wafer at a high throughput. Compared with dry etching processes that require extensively long etching time and single-wafer processing, wet etching is compatible with large-volume batch production, hence allowing high throughput production of high-sensitivity nanopore sensors at a low cost. Additionally, the method provides a process and system that are compatible with conventional process technology without substantial modifications to conventional equipment and processes.

Figure 1:
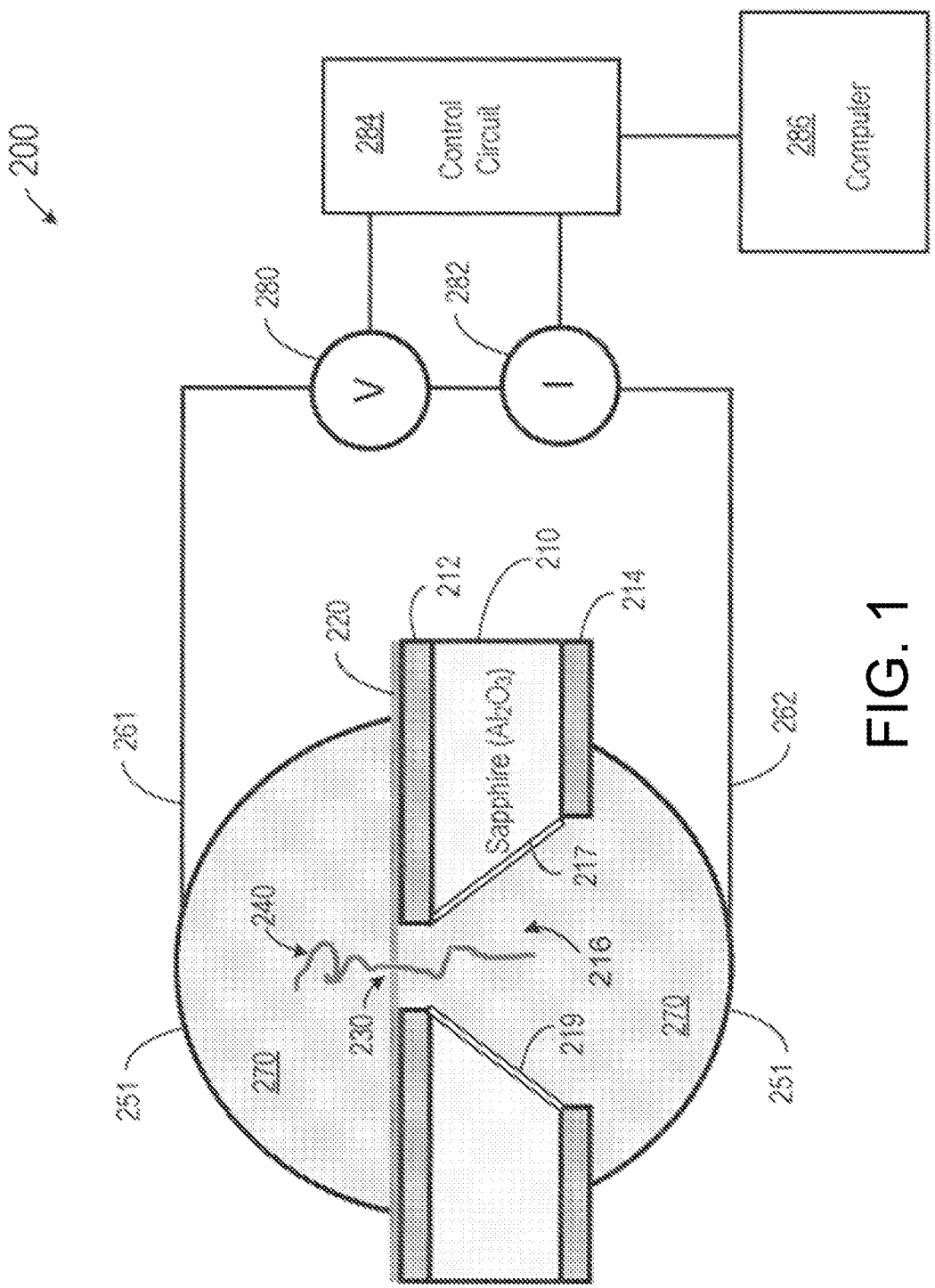
FIG. 1 depicts a simplified model of a sapphire-supported nanopore sensor.

FIG. 1 is a simplified cross-sectional view diagram illustrating part of a solid state nanopore biomolecular sensor based on an insulating substrate according to an embodiment of the present invention. In this embodiment, a sapphire substrate is used as an example of insulating substrates. As shown in FIG. 1, a nanopore device 200 for analyzing biological molecules includes a sapphire substrate 210, and dielectric layers 212 and 214 are disposed on top and bottom surfaces of sapphire substrate 210. A membrane 220 is disposed overlying top dielectric layer 212 on the sapphire substrate. A nanopore 230 is disposed in membrane 220. Sapphire substrate 210 includes a cavity 216. In some embodiments, a dielectric layer 219 is disposed on side surfaces 217 of cavity 216 in the sapphire substrate. A first fluidic reservoir 251 and a second fluidic reservoir 252 are fluidically coupled to nanopore 230.

A first electrode 261 and a second electrode 262 are coupled to an electrically conductive fluid 270 disposed in the first and second reservoirs. The electrodes are configured to impose an electrical potential difference from a voltage supply (V) 280 to conductive fluid 270. As a biomolecule 240 passes though the nanopore channel, it partially blocks the nanopore and thus changes the effective nanopore resistance. This results in a current amplitude change and can also modify the DNA translocation time through the nanopore. These electrical signals can be measured to provide genetic information on the molecule. Nanopore device 200 can also include a current measuring circuit (I) 282 for measuring the current through the nanopore. In this case, a constant voltage can be applied and current measured, which could be an instantaneous measurement or over a period of time (e.g., with an integrating capacitor).

Alternatively, a constant current can be applied to the conductive fluid, and the voltage can be measured to determine changes in the resistance as a biomolecule 240 passes though the nanopore channel. In this case, component 282 (I) can represent a constant current supply, and component 280 (V) can represent a voltage measurement circuit. Further, both current and voltage can vary as well. As long as the current or voltage source is varied in a known or reproducible fashion, the measured electrical signals can be used to identify genetic information of the molecule. Nanopore device 200 can also have a control circuit 284 for controlling the measurement for processing the detected signal. Control circuit 122 may include amplifier, integrator, noise filter, feedback control logic, and/or various other components. Control circuit 122 may be further coupled to a computer 286 for analyzing the signals to determine the components of the molecule, e.g., bases of a DNA molecule.

Embodiments of the present invention provide a method of forming dielectric membranes on insulating sapphire substrate, which is suitable to manufacture nanopore devices. The method can also be implemented using other crystalline insulating substrates having a wet etching selectivity that is crystalline orientation dependent. Embodiments can use an anisotropic chemical etching method to create cavities on a sapphire substrate. Typically, a mixture of sulfuric acid and phosphoric acid is heated to above 250° C. and used for sapphire etching. This etching method results in selective etching c-plane sapphire much faster than other crystal planes. Using such an etching solution, a patterned material layer, e.g. made in $SiO_2$, can be used as an etch mask to effectively protect the sapphire underneath and hence creates a cavity in the region without this protective layer.

By precisely designing the shapes and dimensions of this protective layer (etching mask), embodiments can control the crystal facets on the sapphire substrates, and thus control the lateral dimensions of membrane precisely. This anisotropic wet etching is suitable for batch processing of multiple wafers for large-scale and low cost production, and thus hundreds and even thousands of nanopore membranes can be manufactured at the same time. The mask shape and dimensions can be precisely controlled, hence allowing precise high-yield production. In addition, the sapphire substrate is compatible with Si-based micro and nanofabrication technologies and can be further integrated with other electronic components.

Figure 2:
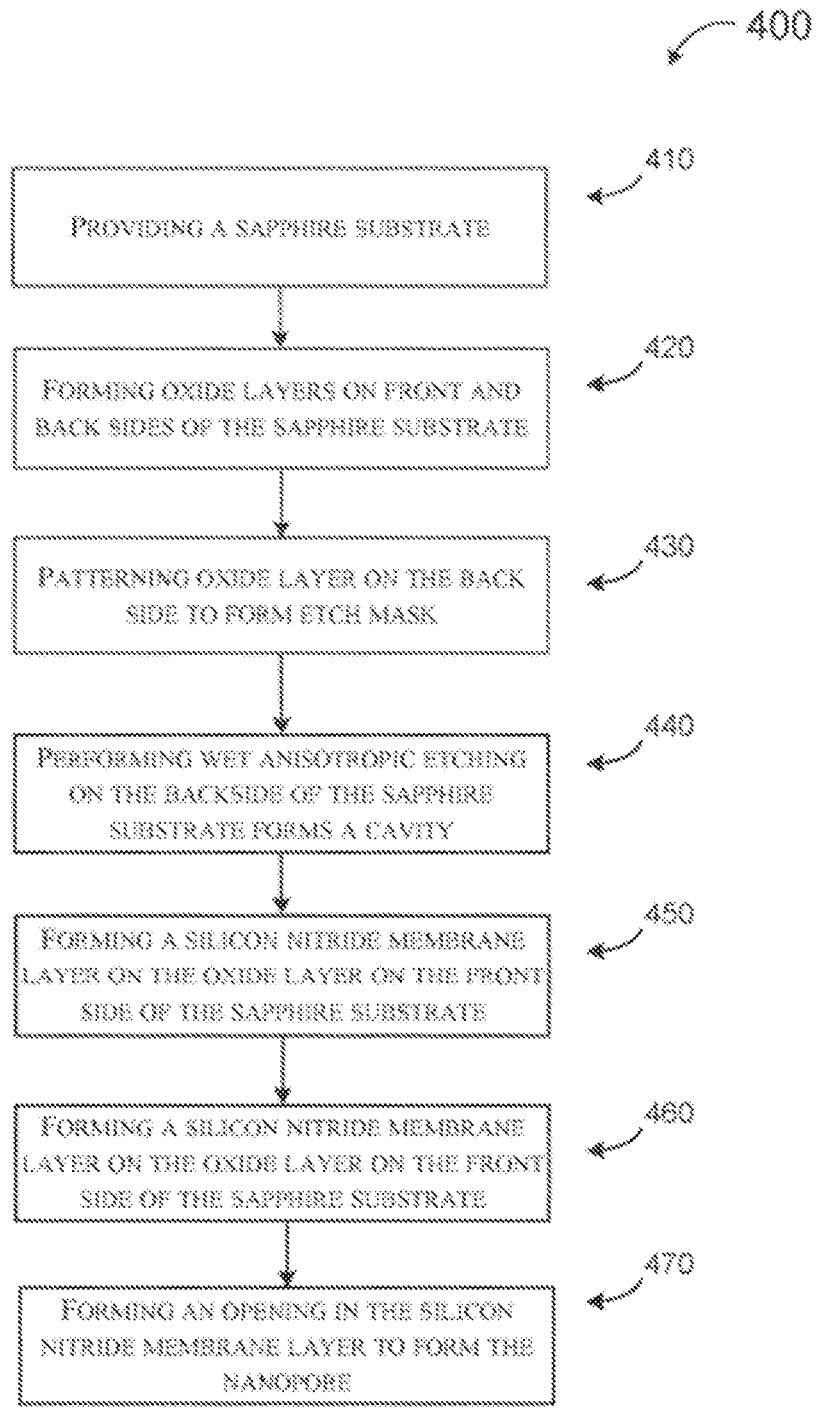
FIG. 2 is a flow chart illustrating a method for forming a nanopore device.

FIG. 2 is a flowchart illustrating a method for forming a nanopore device having a nanopore in a dielectric membrane on an insulating sapphire substrate according to an embodiment of the present invention. The method is briefly summarized here and will be further described below with reference to FIGS. 3A-3G. As shown in FIG. 2, a method 400 forming a nanopore device includes the following steps.

Step 410: Providing a sapphire substrate;
Step 420: Forming oxide layers on front and back sides of the sapphire substrate;
Step 430: Patterning an oxide layer on the back side to form an etch mask;
Step 440: Performing wet anisotropic etching on the backside of the sapphire substrate to form a cavity;
Step 450: Forming a silicon nitride membrane layer on the oxide layer on the front side of the sapphire substrate;
Step 460: Removing the first oxide layer in the cavity such that the silicon nitride membrane layer is suspended over the cavity in the sapphire substrate; and.
Step 470: Forming an opening in the silicon nitride membrane layer to form the nanopore.

FIGS. 3A-3G are simplified cross-sectional view diagrams illustrating the method for forming a nanopore device according to some embodiments of the present invention. The method is described below with reference to the flowchart in FIG. 2 and FIGS. 3A-3G. The same reference numerals are used in FIGS. 3A-3G- to identify common components as the nanopore device 200 in FIG. 1.

Figure 3A:
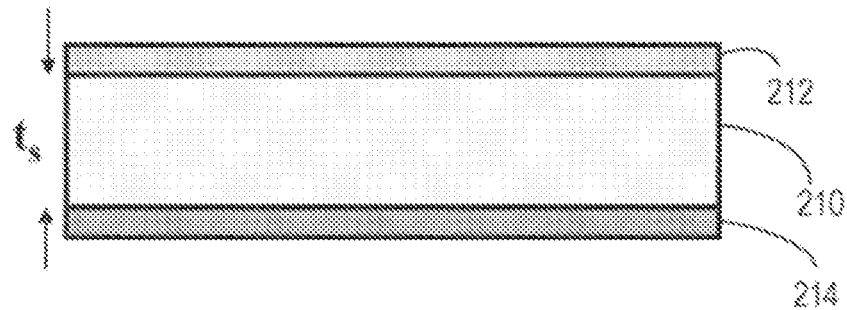
FIGS. 3A-3G are cross-sectional views illustrating a method for forming a nanopore device.

At step 410 of method 400 in FIG. 2, a sapphire substrate 210 is provided as shown in FIG. 3A.

At step 420, as shown in FIG. 3A, a first dielectric layer 212 is formed on a front side of sapphire substrate 210, and a second dielectric layer 214 is formed on a back side of sapphire substrate 210. These dielectric layers can be made of the same material or different materials, and they can be deposited in the same process step or different steps. For example, the first dielectric layer 212 and the second dielectric layer 214 can both be a layer of silicon dioxide $SiO_2$. In some embodiments, a layer of silicon dioxide $SiO_2$ can be deposited on both sides of the sapphire wafer. Silicon dioxide $SiO_2$ is a chemical compound that is an oxide of silicon and is a common insulating or dielectric material used in the semiconductor industry.

The deposition can be carried by standard processes used in the semiconductor industry, such as low-pressure chemical vapor deposition (LPCVD), plasma enhanced chemical vapor deposition (PECVD), etc. In an LPCVD process, a silicon precursor, such as silane $SiH_4$, and an oxygen source, e.g., $O_2$, are reacted in a low pressure system to form a layer of silicon oxide. In a PECVD process, the activation of plasma enables oxide deposition at lower temperatures. The thickness of such $SiO_2$ mask can be in a range of 10 nm to 10 μm depending on the etching selectivity of the dielectric layers in subsequent etching steps. In the description below, the first dielectric layer 212 and the second dielectric layer 214 will be referred to as the first oxide layer 212 and the second oxide layer 214. It is understood that other dielectric materials can also be used.

Figure 3B:
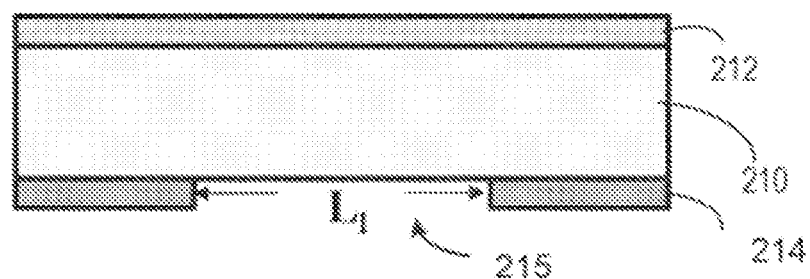

At step 430, as shown in FIG. 3B, the second oxide layer 214 on the backside of sapphire substrate 210 is patterned to form an etching mask having a mask opening 215 in the second oxide layer. The opening can be formed by an etching process using a patterned photoresist layer as a mask. First, photolithography is used to form a mask opening in a photoresist layer. Photolithography uses light to transfer a geometric pattern from a photomask to a light-sensitive chemical material layer (photoresist or resist) on a substrate. The exposure pattern enables the etching of the material underneath the photoresist.

Next, the $SiO_2$ layer can be etched by reactive ion etching (RIE) with the patterned resist mask. As is known in the semiconductor industry, reactive-ion etching (RIE) is a type of dry etching that uses chemically reactive plasma to remove material deposited on wafers. The plasma is generated under low pressure (vacuum) by an electromagnetic field. Under a high voltage, high-energy ions from the plasma attack the wafer surface. The ions can react chemically with the materials on the surface of the wafer, and can also knock off (sputter) some material. Due to the mostly vertical delivery of reactive ions, reactive-ion etching can produce anisotropic etch profiles, such as a vertical profile. In contrast, wet etching is a material removal process that uses liquid chemicals or etchants to remove materials from a wafer. The specific patters are defined by masks on the wafer. Materials that are not protected by the masks are etched away by liquid chemicals.

Unlike dry etching, wet etching is usually isotropic, i.e., the etch rate is the same in all directions. In embodiments of the invention, wet etching of the sapphire substrate is carried out using an anisotropic etching process in which the etch rate depends on the crystalline orientation. After the conclusion of the etch process, the photoresist is stripped using a standard process, e.g., by oxygen plasma ashing. In some embodiments, the mask opening can have a triangular shaped window, such that all sidewalls of the cavity etched in a c-plane sapphire substrate, i.e., sapphire with (0111) orientation, are defined by crystalline facets after the crystalline orientation dependent etch. This design can lead to better etch profile control. Further, the triangular shaped opening can provide more mechanical stability. In FIG. 3B, the mask opening has a width of Li, representing one side of the triangular-shaped window. As described below, the desired dimension of the membrane can be determined by the width of the mask opening.

Figure 3C:
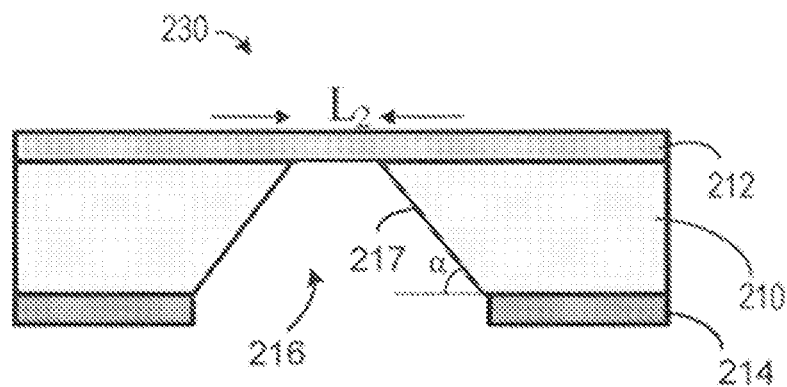

At step 440, as shown in FIG. 3C, the back side of the sapphire substrate is etched using the patterned etch mask to form a cavity 216. This etch is carried out using a wet anisotropic etch that has a crystalline orientation dependent etch selectivity. For example, wet etching of the sapphire can be performed in a mixture of sulfuric acid ($H_2SO_4$) and phosphoric acid ($H_3PO_4$) solutions at an elevated temperature, e.g., a temperature ranging from about 250° C. to about 300° C. Under these etching conditions, the etch rate of sapphire varies with the crystal orientation, and a preferential etching along certain crystalline planes can produce controlled etching profiles. As shown in FIG. 3C, cavity 216 has sloped sidewalls 217 through the sapphire substrate to expose a portion of the first oxide layer 212. The width of the exposed portion of first oxide layer 212 is designated as $L_2$.

Figure 3D:
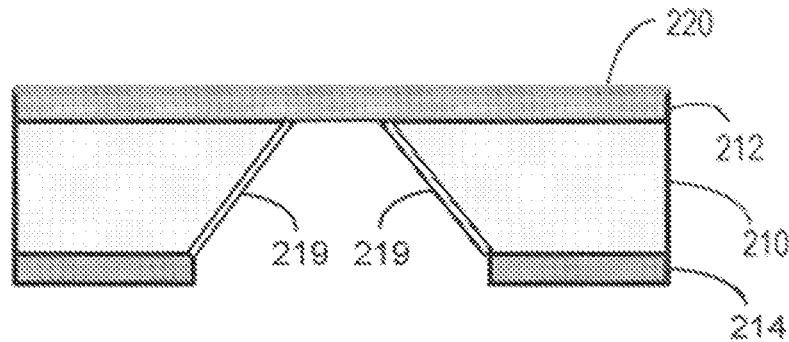

At step 450, as shown in FIG. 3D, a membrane layer 220 is formed on the first oxide layer 212 on the front side of the sapphire substrate. In order to further thin down the effective membrane thickness, a different dielectric material, e.g., silicon nitride ($Si_3N_4$), can be deposited on top of the on the first oxide layer 212. Silicon nitride films are a standard dielectric material in the semiconductor industry. A silicon nitride layer can be formed by a plasma enhanced chemical vapor deposition (PECVD) process as described above using silicon and nitrogen precursors. In some embodiments, the thickness of the silicon nitride layer can be from about 3 nsi to about 50 nm. A silicon nitride ($Si_3N_4$) film and a silicon oxide ($SiO_2$) film can be etched using different wet or dry etch chemistries.

This etching selectivity allows one of the films to be used as a masking layer or an etch stop layer during the etching of the other film. In this example, silicon nitride layer 220 has a desirable etch selectivity with respect to the first oxide layer 212, and the $SiO_2$ can be selectively etched to leave the thin S13N4 layer suspended on sapphire. In some embodiments, a protective layer 219, e.g., a dielectric layer, can be formed on the sidewalls of the cavity. To simplify the drawings, dielectric layers 219 will be omitted in some of the figures described below.

Figure 3E:
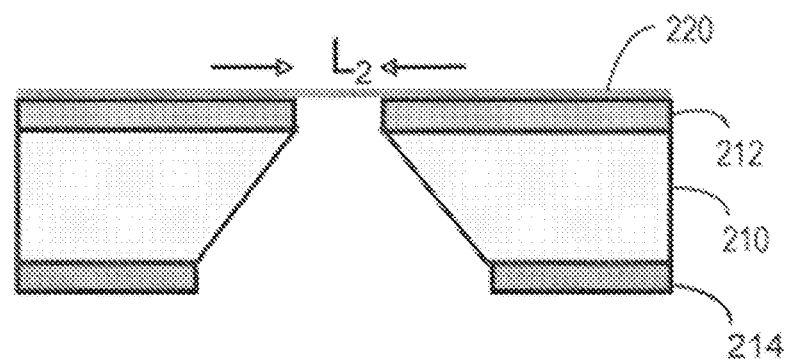

At step 460, as shown in FIG. 3E, the exposed portion of the first oxide layer in the cavity is removed. The first oxide layer can be etched using a fluorine based reactive ion etch (RIE) process or a wet etch process using hydrofluoric acid (IV). Hydrofluoric acid is a solution of hydrogen fluoride (HF) in water and is a standard chemical for wet etching of oxide. The exposed portion of the first oxide layer can be selectively etched without etching the silicon nitride layer. After the exposed oxide is removed, a portion of the silicon nitride membrane layer 220 is suspended over the cavity in the sapphire substrate. In the example of FIG. 3E, the width of the suspended portion of the membrane is shown as $L_2$.

Figure 3F:
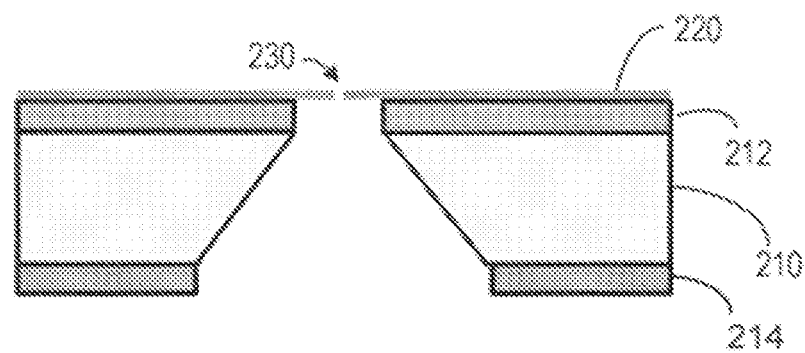

At step 470, as shown in FIG. 3F, a nanopore 230 is formed in the suspended portion of silicon nitride membrane layer 220. Nanopore 230 can be formed by RIE etching through an opening in a masking layer formed by nanolithography such as photolithography or electron beam lithography. In some embodiments, the nanopore can have a size that is configured to allow one nucleic acid molecule to pass through the nanopore. Both photolithography and electron beam lithography can be used to create very small structures in the resist that can subsequently be transferred to the substrate material. Photolithography uses light to transfer a geometric pattern from a photomask to a light-sensitive chemical material layer referred to as a photoresist layer or a resist layer, on the substrate. The exposure pattern enables the etching of the material underneath the photo resist.

In electron-beam lithography, a focused beam of electrons is scanned to draw desired shapes on a surface covered with an electron-sensitive resist film. The electron beam changes the solubility of the resist, enabling selective removal of either the exposed or non-exposed regions of the resist by immersing it in a solvent in a developing process. One advantage of electron-beam lithography is that it can draw patterns (direct-write) with sub-10 nm resolution without using a mask. This form of maskless lithography has high resolution and low throughput. After the mask pattern is formed on the wafer, reactive ion etching can be used to form the nanopore. Alternatively, an opening can be formed in the silicon nitride film using focused electron beam etching to form the nanopore. In this maskless process, an electron beam is used to activate a chemical reaction in selected regions on a wafer to form a nanopore in the membrane film.

Figure 3G:
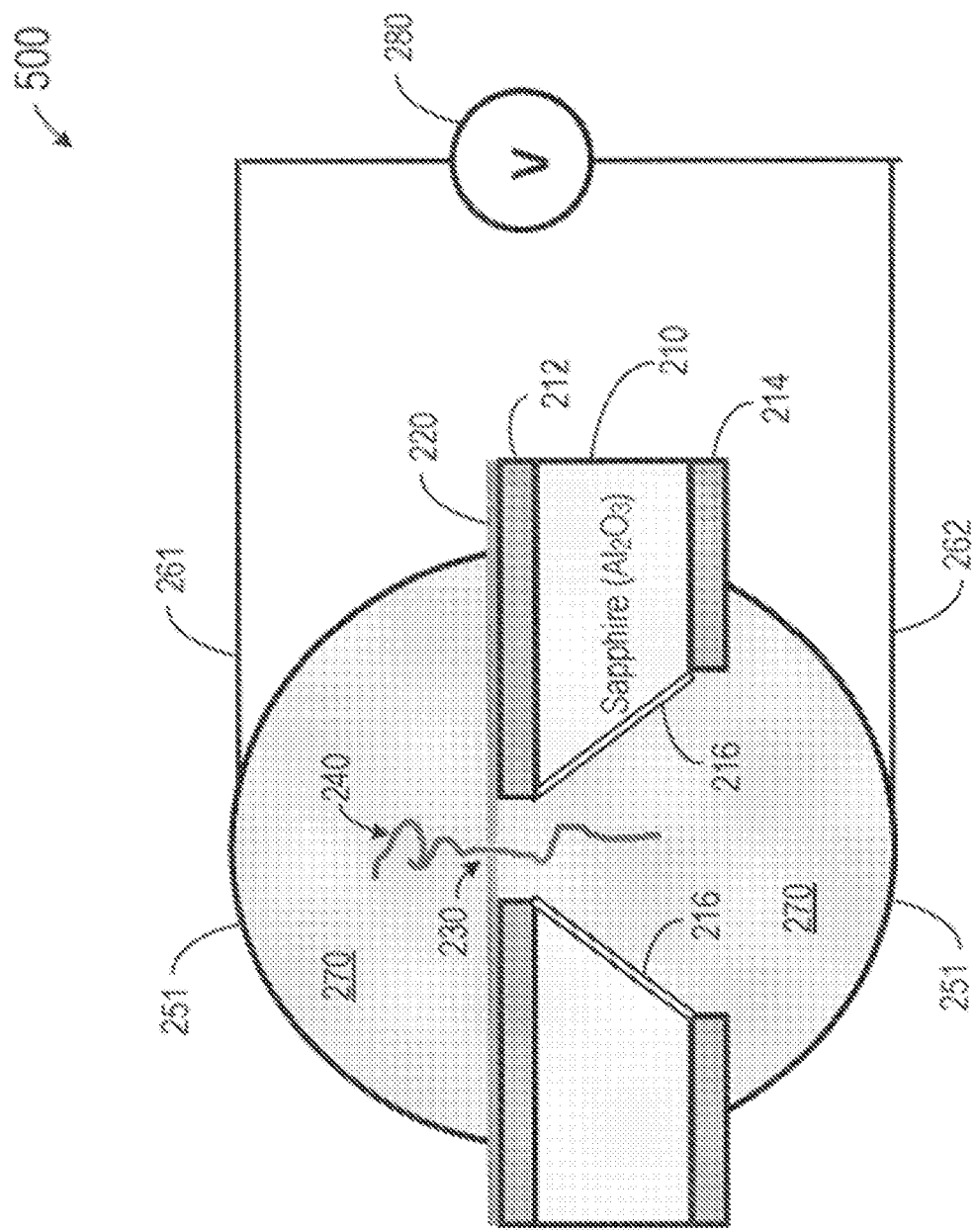

FIG. 3G is a simplified schematic diagram illustrating a nanopore device for analyzing biological molecules using a sapphire substrate based nanopore shown in FIG. 3F. As shown in FIG. 3G, a nanopore device 500 is similar to nanopore device 200 shown in FIG. 1. Nanopore device 500 includes a sapphire substrate 210, and dielectric layers 212 and 214 are disposed on top and bottom surfaces of sapphire substrate 210. A membrane 220 is disposed overlying top dielectric layer 212 on the sapphire substrate. A nanopore 230 is disposed in membrane 220. A dielectric layer 216 is disposed on the side surfaces of a cavity in the sapphire substrate. A first fluidic reservoir 251 and a second fluidic reservoir 252 are fluidically coupled to nanopore 230. A first electrode 261 and a second electrode 262 are coupled to an electrically conductive fluid 270 disposed in the first and second reservoirs. The electrodes are configured to impose an electrical potential difference from a voltage supply V 280 to conductive fluid 270. A biomolecule 240 is shown passing through nanopore 230.

Figure 4B:
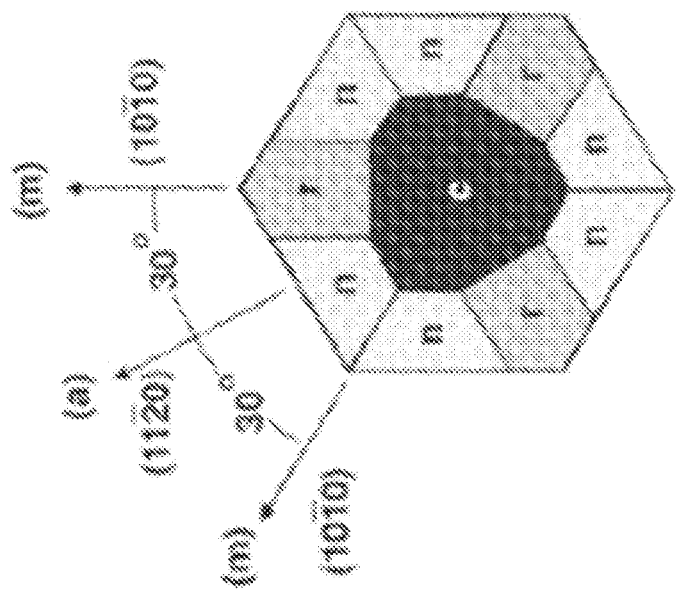
FIG. 4B illustrates a top view of a hexagonal lattice of c-plane sapphire.
Figure 4A:
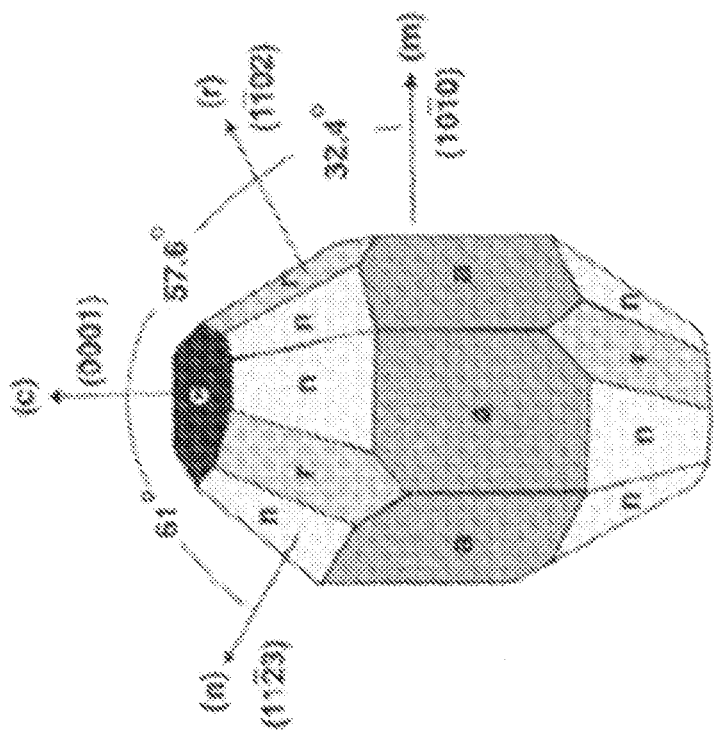
FIG. 4A illustrates a perspective view of a hexagonal lattice of c-plane sapphire.

As described above, in embodiments of the present invention, a method for forming a nanopore device on a sapphire substrate includes anisotropic etching of a sapphire substrate based on different etching rates of various crystalline planes in a sapphire substrate using appropriate wet etching chemicals. FIG. 4A illustrates a perspective view of a hexagonal lattice of c-plane sapphire, and FIG. 4B illustrates a top view of the hexagonal lattice of c-plane sapphire. FIGS. 4A and 4B illustrate various crystalline facets, such as c-plane, a-plane, n-plane, r-plane, etc. As described below, crystalline orientation dependent etching of the sapphire substrate can be used to precisely control the membrane size in the nanopore device structure.

Figure 5A:
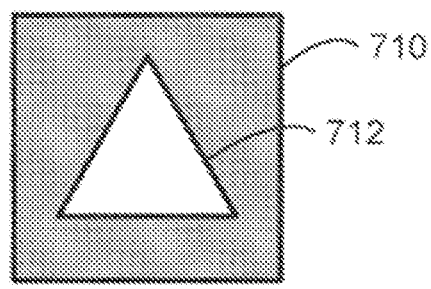
FIGS. 5A-5D illustrate a method of using a triangular etching mask for forming a triangular membrane.
Figure 5B:
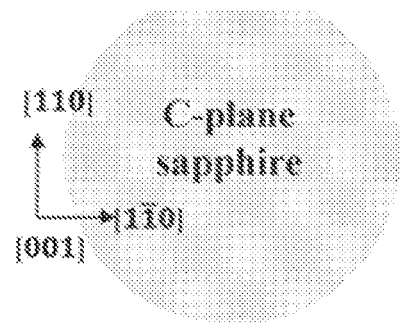
Figure 5C:
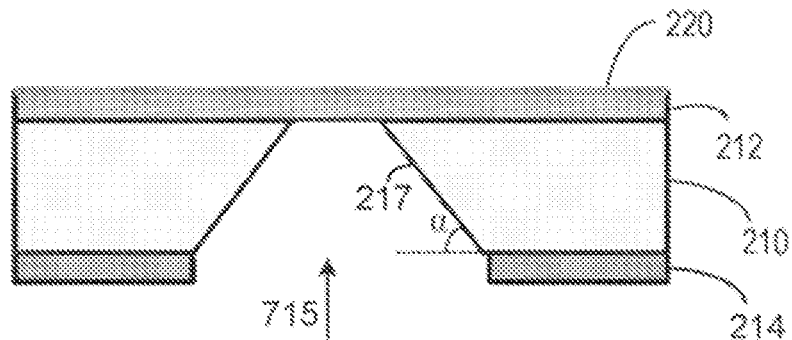

The etching mask can be patterned and aligned to selected crystal orientations of the sapphire substrate for accurate determination of the membrane dimensions. For example, FIGS. 5A-5C illustrate a method of using a triangular-shaped etching mask for forming a triangular-shaped membrane according to some embodiments of the present invention. FIG. 5A illustrates a triangular-shaped etching mask 710 with a triangular opening 712. FIG. 5B illustrates a top view of a c-plane sapphire wafer, which has a top surface in the c-plane. Three crystalline orientations [001], [110], and [110] are also shown.

FIG. 5C is a cross-sectional view illustrating an intermediate structure in the method described above after the sapphire etching process. In FIG. 5C, a sapphire substrate 210 has dielectric layers 212 and 214 disposed on its top and bottom surfaces. A membrane layer 220 is disposed overlying top dielectric layer 212 on the sapphire substrate. As explained above in connection with FIG. 3C, a cavity is formed in sapphire substrate 210 having sidewalls 217, which forms an angle α with a horizontal sapphire surface. As described further below, the angle α is determined by the crystalline orientation dependent etching process.

Figure 5D:
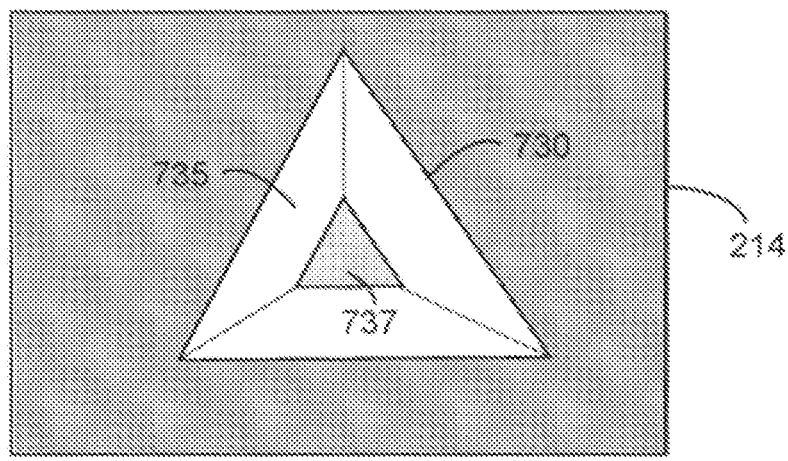

FIG. 5D is a plan view of the device structure in FIG. 5C from the bottom of the sapphire substrate, along the direction of arrow 715. As shown in FIG. 3D, a triangular opening 730 is formed in oxide layer 214 after the oxide layer 214 is etched using a triangular mask, such as mask 710 in FIG. 5A. Sloped sidewalk 735 are etched in the sapphire substrate along crystalline facets that lead to a triangular region 737 in oxide layer 212. In this example, the sides of the triangles in the mask are aligned parallel to or forming 60°/120° angles from [110] direction in the sapphire. As a result, the etching of the sapphire substrate follows the three facets to expose the triangular oxide region. This process provides uniform etching depth control determined by etching along the crystalline facets. Therefore, it is possible to determine the window size of exposed oxide in triangular region 737 based on the size of the triangular opening in the mask layer 710.

Figure 6B:
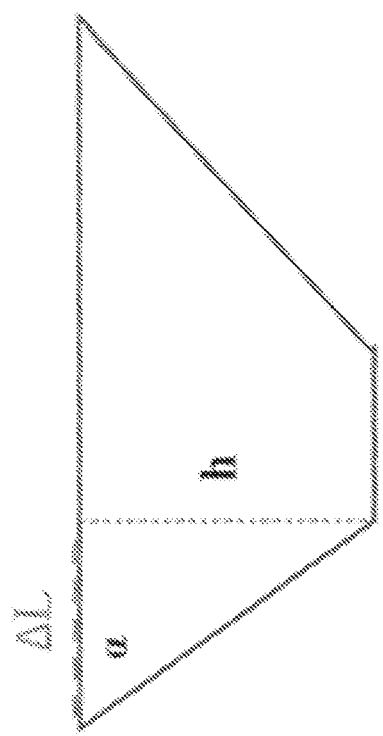
FIGS. 6A and 6B illustrate a method for correlating the triangular sapphire mask window size to the final membrane window size.
Figure 6A:
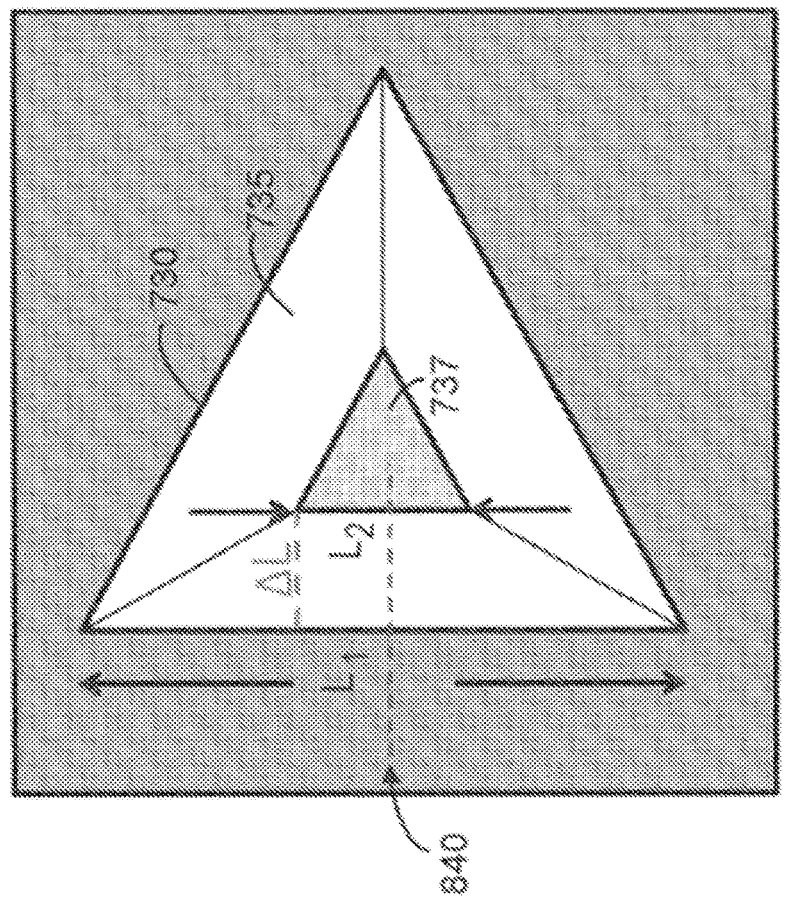

FIGS. 6A and 6B illustrate a method for correlating the triangular-shaped sapphire mask window size to the final membrane window size according to some embodiments of the present invention. This calculation can be used to determine the pattern mask for each customized membrane dimension. FIG. 6A is a top view of an etched cavity in a sapphire substrate, similar to FIG. 5D. Etching the sapphire substrate through the triangular-shaped mask window 730 results in a triangular membrane 737, and the sloped sidewalls 735 are the facets evolved during selective etching.

FIG. 6B is a cross-sectional view along a cut line in FIG. 6A along a dashed line 840. Length Li is the length of a side of the mask window, and $L_2$ is the length of a side of the final membrane. The following relationship results:

$$L_1 = L_2 + 2\sqrt{3}\Delta L$$

with h/L=tan a where a is the angle between the c-plane sapphire and the evolved sidewall facets during etching, and h is the depth of the cavity or the thickness of the sapphire wafer. It follows that the relationship between the etching window sizes can be expressed as follows:

$$= L_2 + 2\sqrt{3}h/\tan \alpha.$$

In the method described above, the depth of the cavity in the sapphire substrate h is the depth of the cavity and is also the thickness of the sapphire substrate, which typically ranges from 100 μm to 1 mm. After determination of the sapphire thickness to be used and the etching angle a, the length of the side of the window in each mask Li can be completely determined based on the desired membrane size $L_2$.

Figure 7:
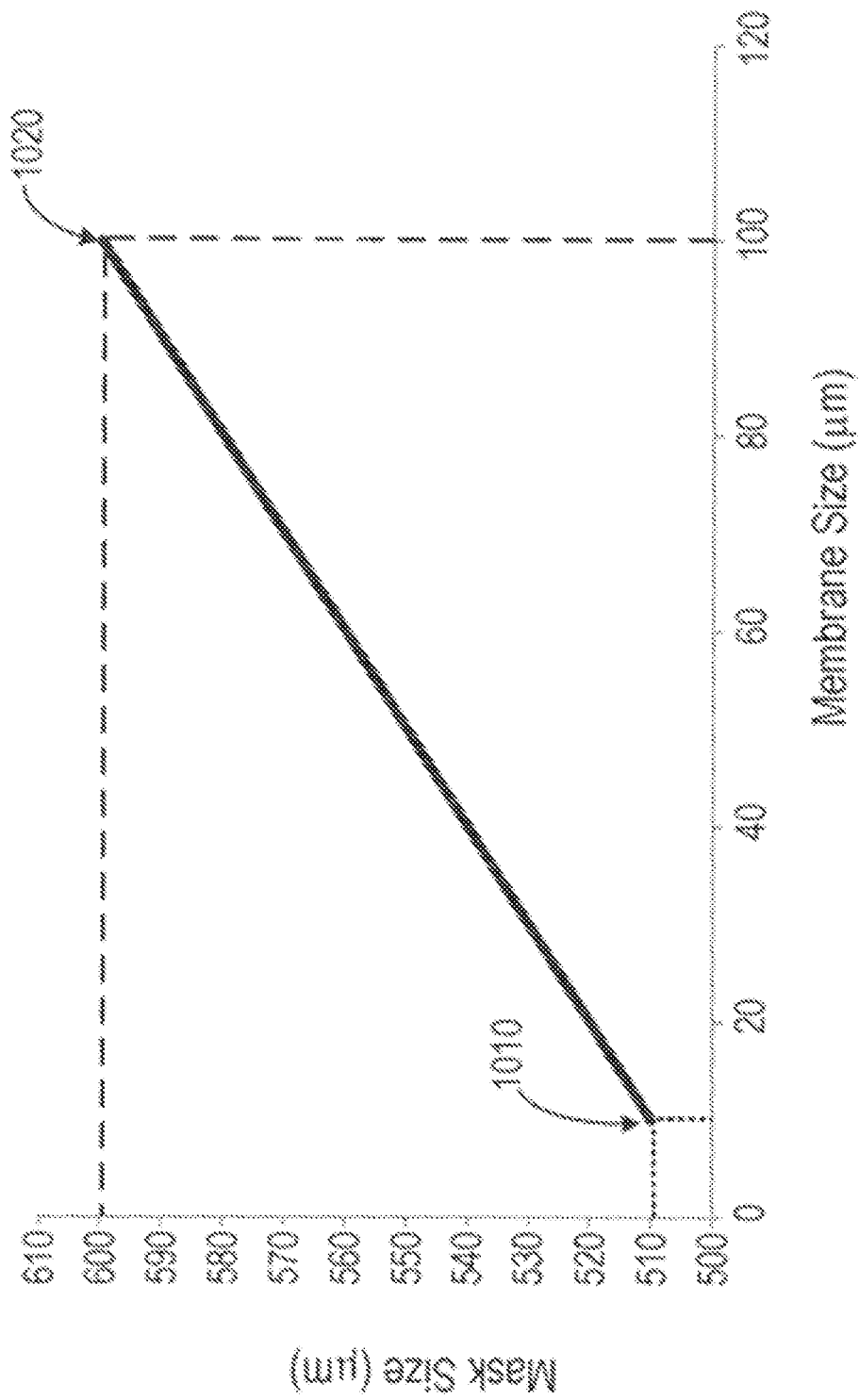
FIG. 7 is a plot illustrating the relationship between the length of a mask window and the side length of a final membrane.

FIG. 7 is a plot illustrating the relationship between the length of mask window and the side length of the final membrane according to some embodiments of the present invention. The plot is derived by plotting Li vs. $L_2$ using the relationship described above, $$= L_2 + 2\sqrt{3}h/\tan \alpha.$$

with a=60° and a sapphire thickness of 250 μm. For example, for a membrane size $L_2$ of about 10 μm, the mask dimension Li can be determined to be about 510 μm, as indicated by data point 1010. To get a lamer membrane size $L_2$ of about 100 μm, the mask dimension $L_1$ can be determined to be around 600 μm, as indicated by data point 1020. This method allows good control of membrane size, which is a factor to controlling the membrane capacitance and the current noise.

The mask window can be a circle or a polygon (e.g., a triangle or a hexagon). The polygon can have a regular or irregular shape.

In some embodiments, the polygon is an equilateral triangle, and an edge of the equilateral triangle is aligned at an offset angle α from a crystalline plane of the sapphire substrate, where 0°<α<60°. The silicon nitride membrane is in the shape of an equilateral triangle when 0°<α<20° and 40°<α<60°. The silicon nitride membrane is in the shape of a polygon (e.g., a nonagon) when 20°<α<40°.

In some embodiments, the polygon is a hexagon. An edge of the hexagon can be aligned at an offset angle α from a crystalline plane of the sapphire substrate, where 5°<α<55°. The silicon nitride membrane is in the shape of an equilateral triangle when 10°<α<35°. An an area of the silicon nitride membrane is substantially constant when 10°<α<35°. Sides of the silicon nitride membrane are parallel to sides of the hexagon when $10°<\alpha<35°$. The silicon nitride membrane is in the shape of an irregular hexagon when $10°>\alpha>35°$. Sides of the irregular hexagon are oriented along particular crystal orientations of the sapphire substrate. Interior angles of the irregular hexagon are between about 90° and 150°.

In some embodiments, the mask opening is in the shape of a circle. When the mask opening is in the shape of a circle, the silicon nitride membrane is polygonal and can have three-fold symmetry. The polygonal silicon nitride membrane has 6 edges.

EXAMPLES

Figure 8A:
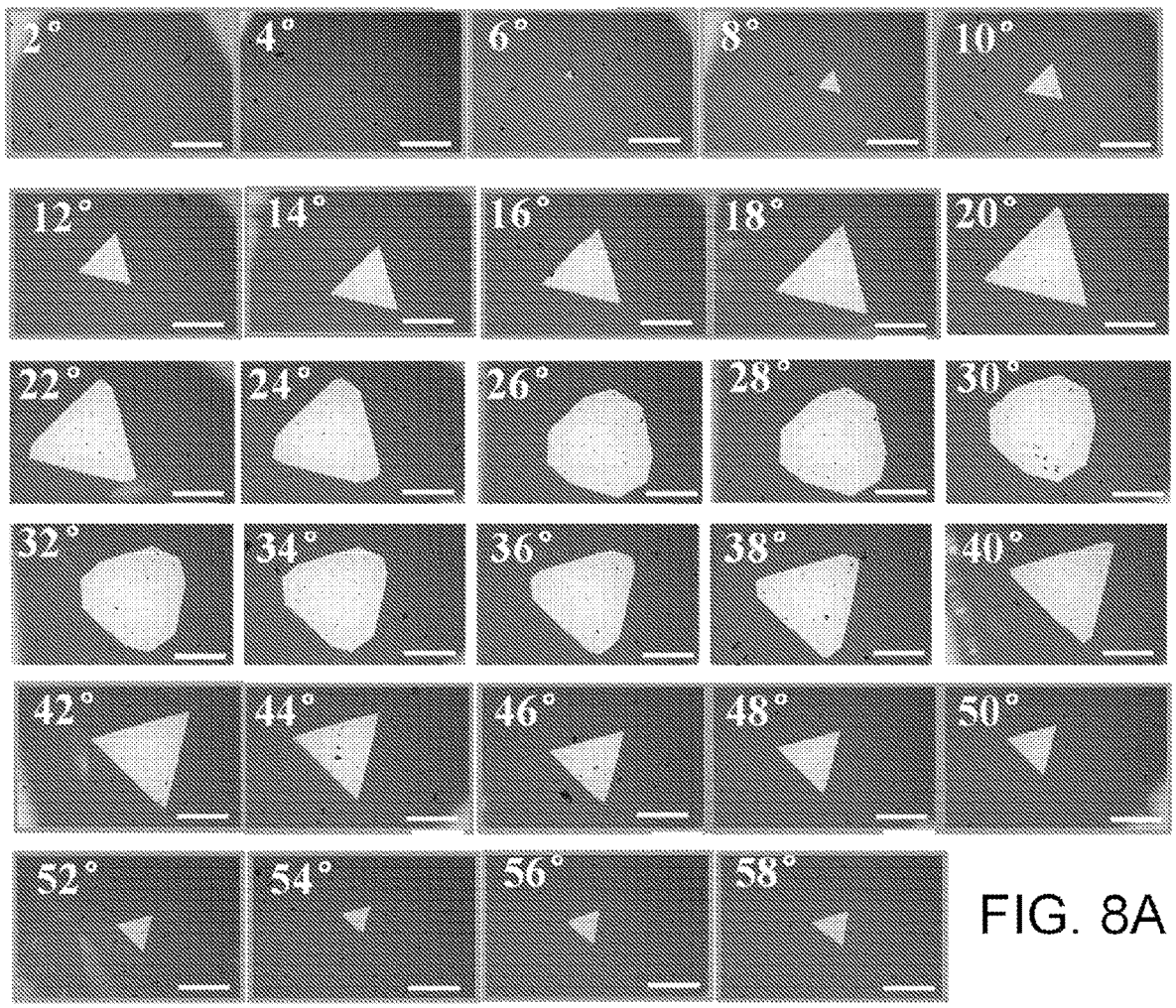
FIG. 8A shows optical images of Sift/sapphire membranes formed with triangular masks with angle $\alpha$ in 2° increments from 2° to 58°.
Figure 8B:
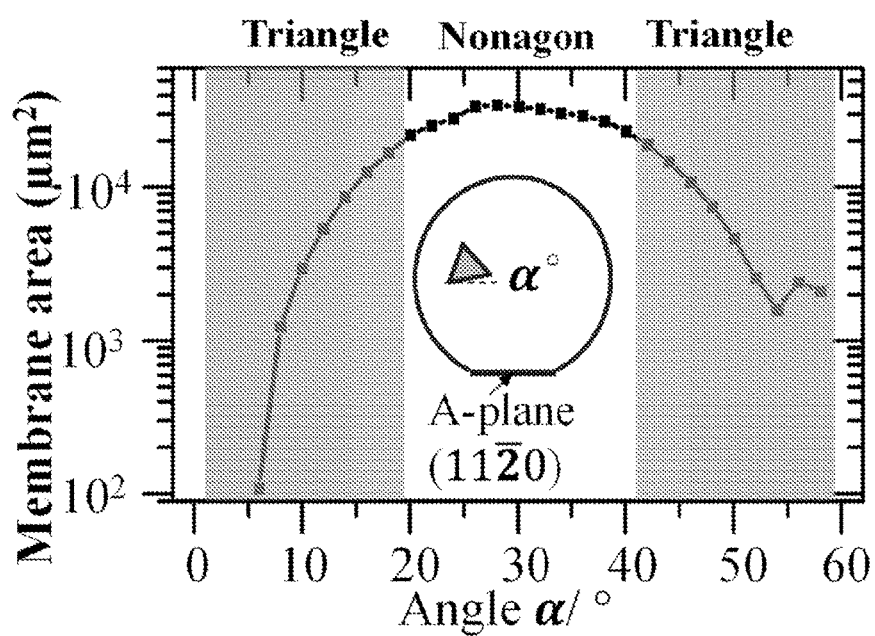
FIG. 8B shows membrane area dependence on the window-to-flat alignment angle $\alpha$.

Triangular Window 2 inch sapphire wafers were lithographically patterned using a desktop laser writer to study the impact of etching window design on the membrane formation. The mask design included triangular etching windows with a rotational alignment angle $\alpha$ between one of the window sides to the A-plane sapphire facet (1120) tuned from $0<\alpha<60°$. Given the six-fold symmetry of sapphire lattice, this test would effectively cover all the possible angles. The accuracy in lithographical crystal alignment was found to be about 2-3°, but the step size of angle increase step was precisely defined by mask layout and set as 2°, thus providing enough information to probe the sapphire facet evolution. FIG. 8A shows images of the membranes formed at alignment angles in 2° increments from $\alpha=2°$ to $\alpha=58°$. FIG. 8B shows membrane area as a function of angle $\alpha$. The membrane geometry was found to be dependent on the window-to-flat alignment angle $\alpha$. For example, two sets of triangular membranes were formed when $-20°<\alpha<20°$ (or equivalently $0<\alpha<20°$ and $40°<\alpha<60°$), with a rotational angle offset between the two at 30°. However, complex polygon membranes with up to nine sides emerged when $20°<\alpha<40°$, where six of the sides were parallel to the sides of two sets of triangular membranes. Second, the membrane area is also sensitive to the angle alignment a. The largest area is $3\times10^4$ $\mu m^2$ or greater, whereas the smallest is only about 100 $\mu m^2$ (i.e., more than three orders of magnitude difference in area and thus the membrane capacitance). On the other hand, given the same mask size, the formed smaller membrane is expected to have a smaller facet angle $\delta$.

According to the results, $\alpha\sim0°$ was chosen to create small membranes on sapphire. Additionally, the triangular mask window size $L_1$ was varied to experimentally establish a relationship between the mask design $L_1$ and the membrane size $L_2$. A plasma enhanced chemical vapor deposition (PECVD) $SiO_2$ layer was deposited and patterned into triangular cavity windows by laser writer and reactive ion etching (RIE). The $SiO_2$ masked etching of 250 $\mu m$ thick 2" diameter sapphire wafers in a mixture of hot sulfuric and phosphoric acids (solution temperature ~300°, with a high selectivity of 500:1. Rectangular dicing marks surrounding the cavity windows were includes during lithography, creating trenches in sapphire after acid etching that allowed the sapphire to be hand-diced into 5 mm by 5 mm square chips. This chip size was designed to fit into a fluidic jig and TEM holder for nanopore drilling and electrical characterization. The formed $SiO_2$ membrane (3 $\mu m$ thick) was found intact during the etching and chip dicing process, with the membrane size $L_2$ tunable in a wide range from 5 to 200 $\mu m$. The correlation between $L_1$ and the measured membrane size $L_2$ was fitted using a theoretical model, and the effective facet angle $\delta\sim50°$ was found. Thus, the fabrication of ultrasmall membranes for functional sapphire chips was demonstrated.

The membrane geometry of the resulting membranes was found to be sensitive to $\alpha$, (i.e., the alignment angle between the triangular mask and the sapphire crystal flat). As a result, an error in a may result in a deviation in membrane size and accordingly adversely affect the accuracy in controlling the device capacitance. Such an effect makes it particularly challenging to create small membranes. In an effort to increase accuracy in controlling the device capacitance, hexagonal etching windows were used.

Hexagonal Window

FIG. 9A shows images of the membranes formed at different alignment angles in 5° increments from $\alpha=0°$ to $\alpha=55°$. It was found surprisingly the hexagonal etching windows created membranes in either irregular hexagons or equilateral triangles. Membrane geometry varies at least in part on a between the hexagonal window and the sapphire flat, with an equilateral triangle regime occurring for $10°<\alpha<35°$ and an irregular hexagon regime for $35°<\alpha<10°$. As shown in FIG. 9B, membrane area was found to be almost constant (e.g., variation of less than $2\times10$ $\mu m^2$) in the equilateral triangle region. Thus, a well-controlled membrane area can be achieved using this hexagonal window design despite lithography alignment errors, which may facilitate reproducible fabrication of membranes even at dimensions as small as <10 $\mu m$. In the equilateral triangle region, the sides of the formed triangular membranes remained parallel to that of the hexagonal windows as a changed (see, e.g., FIGS. 9B and 9C). This suggests the exposed sapphire facets in the cavity form a constant facet angle $\delta$ from the c-plane, which is consistent with the observation that the membrane area stayed almost constant. In the irregular hexagon region, however, the hexagonal sides are not parallel to the patterned windows but oriented along particular crystal orientations, with the interior angles ranging from about 90° and 150°.

The primary facets of sapphire include the c-plane (0001, the wafer surface in these experiments), the A-plane (1120, the facet of the wafers), the M-plane (1010), the N-planes (1123) and R-planes (1102). The M- and A-planes have slow etching rates and are perpendicular to the c-plane, and thus believed less of a factor in the observed cavity formation. In contrast, the R- and N-planes have lower etching rates than the C-plane due to their much higher activation energy (~1.7 eV compared to 1.2 eV for C-plane). Interestingly, by connecting the hypothetical lines intersecting C-planes from the N- and R-facets, polygons resembling the experimentally obtained membranes for both triangular and hexagonal masks can be illustrated. Furthermore, the angles between the intersection lines of N- and R-planes on C-planes were calculated as 30/150° or 90°, the angles between the intersection lines of neighbor R- and R'-planes on C-planes as 60/120°, and the angles between the intersection lines of neighbor N- and N'-planes on C-planes as 60/120°. Comparing to experimental results where the triangular masks created two sets of triangular membranes with a rotational angle of 30/150° to each other, one set was thought to be formed by N-planes and the other by R-planes. Further, the hexagonal masks created polygons with alternating interior angles of 90° and 150° (FIG. 6E), suggesting the facets are mixed R- and N-planes.

Sapphire-Supported (SaS) Nanopore Membrane Fabrication

250 $\mu m$ thick 2-inch c-plane sapphire wafers, purchased from Precision Micro-Optics Inc., were RCA2 cleaned (deionized water: 27% hydrochloric acid: 30% hydrogen peroxide=6:1:1, 70° C.) for 15 min. The RCA2 surface cleaning promotes film adhesion to the substrate, which otherwise can result in film cracking during high-temperature sapphire etching. One to 3 µm silicon oxide (Sift) (thicker is preferred for larger membranes) was then deposited via plasma-enhanced chemical vapor deposition (PECVD, 350° C., deposition rate 68 nm/min) on both sides, followed by photolithography and reactive-ion-etching (RIE) (Plasma-Therm 790, $CHF_3$ based chemistry, etching rate 46 nm/min) to form a triangular etching window in $SiO_2$. Next, hot sulfuric acid and phosphoric acid (3:1, solution temperature ~300° C.) were used to etch through the sapphire wafer (etching rate up to 12 µm/hr) and to suspend the $SiO_2$ membrane. To ensure the safety of handling hot acids, a custom-designed a quartz glassware setup suitable for the high-temperature acid-based sapphire etching process was used. The sapphire wafer was intentionally placed vertically in a 2-inch glass boat in the etching container to minimize possible damage to the membrane from the boiling acids. Acid was added to the quartz glassware, and then loaded the 2-inch glass boat with the wafer into the quartz glassware. A clamp seal and a condenser column were then installed on top of the glassware to minimize acid vapor leakage. The etching rate was chosen to be relatively slow in this customized container to minimize wafer breakage during etching; however, further increasing the solution temperature is an option to exponentially increase the etching rate and thus allow for larger throughput.

Following sapphire etching, the $SiO_2$ membrane was thinned down as needed by RIE to <1.5 µm. This was followed by depositing a layer of silicon nitride (SiN) (30-300 nm) onto the $SiO_2$ membrane via low-pressure chemical vapor deposition (LPCVD) (Tystar TYTAN 4600, 750° C., deposition rate: 6 nm/min). The unintentionally deposited SiN in the back cavity of the chip was removed by RIE. Next, hydrofluoric acid (8%) was used to etch the $SiO_2$ layer (90 nm/min) to suspend the SiN layer. The final SiN membrane was thinned down as needed by hot 85% phosphoric acid (etching rate ~2.5 nm/min) to desired thickness.

The thicknesses of membranes were determined by optical reflectance measurement (Filmetrics F40) and by subsequent fitting. An experimentally measured refractive index of the SiN films on a Si monitor sample (Woollam Spectroscopic Ellipsometer) was used to improve fitting accuracy.

For comparison, SiS nanopore membranes were purchased from SiMPore Inc. The chips were made from 100 mm diameter, 200 µm thick, float-zone Si wafer (resistivity of 1-10 Q·m) with-100 nm thermal $SiO_2$ and-20 nm LPCVD SiN films, where the thermal $SiO_2$ from the cavity side was removed to produce an array of suspended SiN membranes of 4-5 µm in diameter. The $SiO_2$ and SiN film thicknesses were confirmed by M-2000 ellipsometer (J.A. Woollam Co.) as 99 nm and 23 nm, respectively.

A JEOL 2010F transmission electron microscope (TEM) was used to drill the nanopores. The 5 mm by 5 mm nanopore chips were diced and placed in a customized TEM sample holder. The largest condenser aperture and beam spot size were used for maximum beam current output. After alignment, imaging magnification was maximized (1.5M), followed by 5-15 min beam stabilization. The focus was re-adjusted when beam drifting was severe; beam stabilization was then re-monitored at maximum magnification. Upon stabilization, the beam spot was reduced to ~7 mm and rounded by adjusting the condenser astigmatism. Under the conditions of 7.01 kV anode A2 (focusing anode), 3.22 kV anode A1 (extraction anode), and 30 nm SiN membrane, it typically took 75-90 sec to drill through the membrane.

The TEM-drilled nanopore chip was treated with UV ozone cleaner (ProCleaner™, BioForce Nanosciences Inc.) for 15 min to improve hydrophilicity. The chip was then mounted onto a customized flow cell. A solution of 1:1 mixed ethanol and DI water was injected into the flow cell to wet the chip for 30 min. The solution was subsequently flushed away by injection of DI water. Next, 100 mm KCl was injected into the flow cell to test the current-voltage (IV) curve using an Axopatch 200B amplifier and a Digidata 1440A digitizer (Molecular Devices, LLC.). A 1M KCl solution was injected for characterization of the device current.

For DNA sensing, 1 k bp dsDNA (Thermo Scientific NoLimits) was diluted using 1M KCl to 5 ng/µL. $Poly(A)_{40}$ ssDNA (Standard DNA oligonucleotides, Thermo Fisher Scientific Inc.) was diluted using 1M KCl to 50 nm, followed by brief vortex mixing. The DNA solution was injected into the flow cell to collect DNA signals under a 10 kHz and 100 kHz low-pass filter with a sampling frequency of 250 kHz at 50, 100, and 150 mV bias voltages. The flow cell was kept in a customized Faraday cage on an anti-vibration table (Nexus Breadboard, Thor labs) to minimize the environment noise during measurement. The DNA signals were observed and recorded with the Clampex software. Finally, an edited MATLAB program was used to convert all the .abf files to .mat files. All the collected DNA signals were then imported to an OpenNanopore program to generate the dwelling time and blockade current amplitude data of each DNA signal for subsequent analysis.

Suspended dielectric membranes were created on sapphire by anisotropic wet etching. PECVD-deposited $SiO_2$ was used here due to its high-selectivity in masking sapphire etching, which was experimentally determined to be over 500:1. Considering the three-fold symmetry of sapphire crystal, triangular shaped $SiO_2$ etching masks were patterned. Alignment angle of the masks and the sapphire crystal (denoted a) was varied between 0° and 60°, and membrane evolution was monitored. Triangular membranes formed when $0<\alpha<20°$ and $40°<\alpha<60°$. The two sets of triangles were offset by a rotational angle of ~30°. In contrast, complex polygon membranes with up to nine sides emerged when $20°<\alpha<40°$. Additionally, the membrane area was found sensitive to a, yielding an area of more than three orders of magnitude larger when $\alpha\sim30°$ compared to $\alpha\sim0°$.

Since sapphire essentially eliminates the stray capacitance through the substrate, the membrane capacitance of the SaS chips, which is highly dependent on membrane area and thickness, largely determines the total chip capacitance and high-frequency noise. Fabrication of micrometer-sized membranes that are attractive for picofarad sensor capacitance and low-noise biosensing are demonstrated. To guide the mask layout design, theoretical calculations were performed to study the relationship between the membrane and the mask dimensions while keeping $\alpha=0+$. The membrane triangle length $L_2$ could be engineered by the mask triangle length $L_1$ following $$L_1 = L_2 + \frac{2\sqrt{3}h}{\tan\theta},$$

where h is the sapphire wafer thickness and θ is an effective angle between the exposed facets in the cavity and sapphire c-plane that can be empirically determined. By designing $L_1$ from ~750 µm to ~900 µm, modulation of the $SiO_2$ membrane size $L_2$ was demonstrated within a wide range, from 5 to 200 µm.

By fitting the experimental data with a theoretically calculated $L_1$-$L_2$ relationship, it was estimated that a good empirical value for facet angle 9 is ~50°. Based on this knowledge, $L_1$ was designed as 760, 762, 764, and 766 μm and α~0° for wafer-scale fabrication of <20 μm size membranes, which are attractive for picofarad sensor capacitance and low-noise biosensing. Etching two 2-inch sapphire wafers in the same batch, no wafer or membrane breakage was discovered, and 116 suspended micron-sized membranes were obtained, while having 4 membranes not yet completely etched through. It was believed that further etching would eventually create these 4 membranes while slightly enlarging the existing ones due to slower lateral etching on exposed facets. From intentionally patterned rectangular dicing marks surrounding the cavity etching windows, trenches were formed in sapphire wafers after acid etching, allowing even-hand dicing of 5 mm square chips despite the hexagonal crystal structure of sapphire. Importantly, this wafer-scale demonstration strongly indicated the scalability of the membrane formation process, which is crucial to future large-scale, cost-effective sensor fabrication.

When compared to the best available low-noise SiS chips and glass-supported chips that typically have a membrane capacitance of <10 pF, SaS chips were found to be competitive in their expected small capacitance and corresponding capacitive noise. Noticeably, the low-noise SiS and glass chips all require very complicated fabrication processes. For example, the SiS membranes need to be very carefully engineered to reduce the membrane area and introduce thick insulating layers, demanding processes involving nano-lithography, bonding, film deposition, etching, and even silicone painting.

A challenge in fabricating glass chips lies in the reproducibility of creating small membranes on glass, at least in part because bulk and isotropic etching of amorphous glass in hydrofluoric acids (HF) can have poor dimension control while RIE etching is typically only applicable at single-wafer or single-chip level with drastically lowered throughput and increased manufacturing cost. Although combining femto-second laser ablation with LPVCD and chemical wet etching could form glass chips with a ~2 pF device capacitance, it remains unclear how the membrane uniformity (e.g., variation 5 to 40 μm), fabrication throughput, and yield are affected by process fluctuation in laser ablation and chemical etching. The wafer-scale SaS chip design and fabrication strategy presents a scalable manufacturing alternative to the prevalent manufacturing processes of low-noise sensors that are complicated, time-consuming, low-yield, and costly.

The observed membrane size variation within the wafer could be attributed to a few factors. First, the sapphire wafers were found slightly thinner (~1 μm) at the edge than at the center, which could cause membrane enlargement at the edge. Second, the customized hot-plate based etching apparatus could leave a temperate gradient in the acid bath that could affect the etching rate. Further, acid convection under boiling condition may produce local variation in acid concentration and etching rate. In addition, the complex evolution of sapphire facets, currently not fully understood but thought to be due to the competition between R- and N-planes of the sapphire crystals, could be sensitive to crystal orientation alignment and the etching bath conditions. In future studies, the membrane uniformity could be improved by compensating etching window sizes over the wafer, utilizing an etching system that provides better temperature control and acid circulation, and further studying the etching mechanism and optimizing the etching window designs.

Using the triangular $SiO_2$ membranes formed by sapphire etching, a process to create thin SiN membranes suitable for nanopore formation and DNA sensing was developed. Briefly, low-stress LPCVD SiN film was deposited on suspended $SiO_2$ membranes, and then the $SiO_2$ film was removed via selective dry etching and HF based wet etching from the cavity side. The use of SiN film allows precise control of the membrane thickness and minimizes the impact of $SiO_2$ film stress on the membrane structural integrity. The SiN film can be further thinned down to desired thickness when necessary by either RIE and/or wet etching in hot phosphoric acid. RIE could cause non-uniformity and might damage the membrane, causing current leakage, as shown by current-voltage (IV) characteristics. In contrast, wet etching in hot phosphoric acid yielded uniform SiN membrane without current leakage, and thus could be preferable for a DNA sensing test. A nanopore was drilled in the SiN membranes on the sapphire chip (and the float-zone Si chip using TEM for electrical characterization and DNA sensing.

The device capacitance of the SaS and SiS nanopore chips was characterized. Noticeably, the SaS nanopore chip had a 100 times larger membrane area ($L_2$=68 μm, or 2000 μm² in area) than the SiS chip (4.2×4.7 μm square, or ~20 μm²) and slightly thicker SiN (measured 30 nm for sapphire and ~23 nm for Si). The membrane capacitance $C_m$ was estimated at 3.8 pF for the SaS chip, >70 times greater than that of the SiS chip (0.05 pF), following $$C_m = \varepsilon \frac{A}{d},$$

where E is the permittivity of SiN, and A the membrane area and d membrane thickness. Experimentally, $C_m$ was found ~10 pF for the SaS chip, with a deviation from theoretical value possibly attributed to slightly smaller SiN thickness in reality, and much smaller than that of the SiS chip (~1.3 nF) because of the stray capacitance from Si substrate. Considering SaS and SiS nanopores that both have only the simplest membrane structure, insulating sapphire was demonstrated to reduce or eliminate the dominant capacitance resulting from Si substrate conductivity, thus appealing to low-noise measurement.

The ionic current noise for the SaS nanopore, the SiS nanopore, and the open-headstage system (Axopatch 200B) was assessed under 10 kHz and 100 kHz low-pass filter. The root-mean-square (RMS) of the measured current of the SaS nanopore chip is ~5 and 18 pA using 10 and 100 kHz filters, which is only slightly higher than the open-headstage system RMS noise (3 and 11 pA), and yet much better than those from the SiS nanopores (~16 and 46 pA). In comparison, the best reported silicone-painted SiS chips that utilized a locally thinned membrane (0.25 μm² area and 10-15 nm thick in the center) produced ~7 and ~13 pA noise current at 10 kHz and 100 kHz, measured by an optimally designed amplifier that outperforms Axopatch 200B in high-frequency recording. Glass-supported nanopore chips with micro-membranes (25 μm², 70 pF and 314 μm², —2 pF) demonstrated ~13 and ~19 pA noise current at 10 kHz bandwidth, which is approximately 3-4 times larger than the SaS chip. A comparison of noise current from glass-supported nanopore chips showed that the SaS chips are successful in suppressing the noise current.

Additionally, analysis of the power spectral density (PSD) further demonstrates that the SaS nanopores outperformed the SiS chips, particularly at high bandwidth (e.g., >10 kHz) due at least in part to the significantly reduced device capacitance. In the moderate frequency range (e.g., 100 Hz to 10 kHz), the noise power of the SaS nanopore was about one order of magnitude smaller ($\sim 10^{-3}$ pA$^2$/Hz) than that of the measured SiS nanopore ($\sim 10^{-2}$ pA$^2$/Hz) and one order of magnitude smaller or comparable to the glass chips and low-noise SiS chips ($10^{-2}$~$10^{-3}$ pA$^2$/Hz), partly attributed to lower dielectric noise and Johnson noise. Sapphire has a very small dissipation factor D ($\sim 10^{-5}$), two to five orders of magnitude smaller than that of typical borosilicate glass ($10^{-3}$ to 10') and Si (1-100) and comparable to that of high-purity fused silica ($\sim 10'$). Such a small dissipation factor, together with its small device capacitance, is favorable for minimizing noise related to dielectric loss $S_D \propto DC_{chip}f$, where $C_{chip}$ is nanopore chip capacitance and f is the frequency. Additionally, the high resistivity of sapphire (>$10^{14}$ Ω·cm) also served to minimize resistance-related Johnson noise.

To evaluate the performance of DNA molecule detection capability of the SaS nanopore, 1 k bp ds-DNA were translocated through the SaS and the SiS nanopores at 100 kHz) and 10 kHz low-pass filters under 50 mV, 100 mV, and 150 mV bias, respectively. By comparing representative ionic current traces of 1 k bp dsDNA, it was observed that the DNA signals collected by the SiS nanopore displayed severe signal distortion, particularly at lower bias voltages. These irregular signals, together with the high baseline noise, made it challenging to faithfully distinguish DNA signals from the background. In comparison, the SaS nanopore produced easily distinguishable DNA signals with much less distortion or noise at as high as 100 kHz bandwidth. Additionally, low-frequency recording, e.g., at 10 kHz, would result in serious data loss of fast DNA signals, thus presenting only longer and in some occasions distorted signals. Thus, the SaS nanopores were found to enable high-speed, high-throughput, and high-fidelity detection of DNA signals.

To study the DNA translocation mechanism from the SaS chip, the DNA signals were extracted using the OpenNanopore Program, and then scatter-plotted the fractional blockade current $I_B(=i_b/i_0)$ and the dwelling time $\Delta t$ of all the DNA events under 50 mV. Here $i_b$ is the blocked-pore current and $i_0$ is the open-pore current. The use of $I_B$ allows us to eliminate the impact of bias difference on DNA signal analysis. Two distinct populations were observed and recognized as the translocation events and the collision events. Further, the current blockade distribution was analyzed and fitted with Gaussian function, producing two distinct $I_B$ populations attributed to translocation and collisions. The dwelling time $\Delta t$ of each of the two event populations was analyzed and fitted with exponential decay function. This showed that the translocation events had a longer tail (decay constant 16.19 µs) than the collision events (decay constant 8.45 µs).

This signal segregation approach was further applied to analyze all the DNA signals collected from the SiS and SaS nanopores. By scatter-plotting the normalized DNA blockade signal ($1-I_B=\Delta I/i_0$) and marking the normalized current noise ($I_{RMS}/i_0$, dash-dot lines) at each bias voltage (50 mV, 100 mV, 150 mV), the SNR (defined here as $$\frac{\Delta I}{I_{RMS}} = \frac{1-I_B}{I_{RMS}/i_0}$$

of the true DNA translation signals was investigated. The SaS nanopores are seen to produce slightly smaller DNA signal amplitude than SiS nanopores because of their larger pore size and thicker membrane. Noticeably, given the suppressed noise current, the SaS nanopore still evidently outperformed the SiS nanopore in SNR. For example, the SaS nanopore has a SNR of 21 at 150 mV bias, almost twice as good as the SiS nanopore with a SNR of 11. Generally smaller nanopore and thinner membrane are preferred for optimal signals and SNRs. Experimental data illustrated the impact of pore sizes on the DNA signals for both SiS (e.g., 4 nm, 7 nm) and SaS (e.g., 7 nm, 20 nm) nanopore chips (FIG. S11). Additionally, thinner SiN (e.g., down to 5 nm) and few-layer to monolayer 2D materials are believed to improve the signal and SNR.

Detection of short single-stranded (ss) DNA molecules using SaS nanopores was attempted. Ionic current traces of Poly(A)$_{40}$ ssDNA translocation events were recorded under 100 kHz low-pass filter with the voltages from 100 mV to 150 mV. The same analysis was performed to investigate the SNR of this ssDNA, and a SNR of ~6 was obtained for both 100 mV and 150 mV bias voltages. This provided evidence that the SaS nanopores can detect a wide range of biomolecules of different sizes. It is believed that SNR can be enhanced by using thinner membrane thickness and smaller nanopores.

Although this disclosure contains many specific embodiment details, these should not be construed as limitations on the scope of the subject matter or on the scope of what may be claimed, but rather as descriptions of features that may be specific to particular embodiments. Certain features that are described in this disclosure in the context of separate embodiments can also be implemented, in combination, in a single embodiment. Conversely, various features that are described in the context of a single embodiment can also be implemented in multiple embodiments, separately, or in any suitable sub-combination. Moreover, although previously described features may be described as acting in certain combinations and even initially claimed as such, one or more features from a claimed combination can, in some cases, be excised from the combination, and the claimed combination may be directed to a sub-combination or variation of a sub-combination.

Particular embodiments of the subject matter have been described. Other embodiments, alterations, and permutations of the described embodiments are within the scope of the following claims as will be apparent to those skilled in the art. While operations are depicted in the drawings or claims in a particular order, this should not be understood as requiring that such operations be performed in the particular order shown or in sequential order, or that all illustrated operations be performed (some operations may be considered optional), to achieve desirable results.

Accordingly, the previously described example embodiments do not define or constrain this disclosure. Other changes, substitutions, and alterations are also possible without departing from the spirit and scope of this disclosure.

What is claimed is:

1. A method of fabricating a nanopore sensor, the method comprising:
   depositing a first oxide layer on a first side of a sapphire substrate and a second oxide layer on a second side of the sapphire substrate opposite the first side;
   patterning the second oxide layer to form an etch mask having a mask opening in the second oxide layer;

performing a crystalline orientation dependent wet anisotropic etch on the second side of the sapphire substrate using the etch mask to form a cavity having sloped side walls through the sapphire substrate to yield an exposed portion of the first oxide layer, each of the sloped side walls being a crystalline facet aligned with a respective crystalline plane of the sapphire substrate;

depositing a silicon nitride layer on the first oxide layer;

removing the exposed portion of the first oxide layer in the cavity, thereby defining a silicon nitride membrane in the cavity; and forming an opening through the silicon nitride membrane, wherein the opening is a nanopore with a diameter in a range of 1 nm to 20 nm, wherein the mask opening is in the shape of an equilateral triangle, and an edge of the equilateral triangle is aligned at an offset angle $\alpha$ from a crystalline plane of the sapphire substrate, and wherein the silicon nitride membrane is in the shape of a nonagon when for $20°<\alpha<40°$.

2. The method of claim 1, wherein the etch is conducted at a temperature in a range between 150° C. and 450° C.

3. The method of claim 1, wherein a dimension of a surface of the sapphire substrate is in a range between about 1 mm and about 20 cm and a thickness of the sapphire substrate is in a range between about 0.1 mm and about 1 mm.

4. A method of fabricating a nanopore sensor, the method comprising:

depositing a first oxide layer on a first side of a sapphire substrate and a second oxide layer on a second side of the sapphire substrate opposite the first side;

patterning the second oxide layer to form an etch mask having a mask opening in the second oxide layer;

performing a crystalline orientation dependent wet anisotropic etch on the second side of the sapphire substrate using the etch mask to form a cavity having sloped side walls through the sapphire substrate to yield an exposed portion of the first oxide layer, each of the sloped side walls being a crystalline facet aligned with a respective crystalline plane of the sapphire substrate;

depositing a silicon nitride layer on the first oxide layer;

removing the exposed portion of the first oxide layer in the cavity, thereby defining a silicon nitride membrane in the cavity; and forming an opening through the silicon nitride membrane, wherein the opening is a nanopore with a diameter in a range of 1 nm to 20 nm, wherein the mask opening is in the shape of a hexagon, and wherein an edge of the hexagon is aligned at an offset angle $\alpha$ from a crystalline plane of the sapphire substrate, where $5°<\alpha<55°$.

5. The method of claim 4, wherein the etch is conducted at a temperature in a range between 150° C. and 450° C.

6. The method of claim 4, wherein a dimension of a surface of the sapphire substrate is in a range between about 1 mm and about 20 cm and a thickness of the sapphire substrate is in a range between about 0.1 mm and about 1 mm.

7. The method of claim 4, wherein the silicon nitride membrane is in the shape of an equilateral triangle for $10°<\alpha<35°$.

8. The method of claim 7, wherein an area of the silicon nitride membrane is constant for $10°<\alpha<35°$.

9. The method of claim 7, wherein sides of the silicon nitride membrane are parallel to sides of the hexagon for $10°<\alpha<35°$.

10. The method of claim 4, wherein the silicon nitride membrane is in the shape of an irregular hexagon for $5°<\alpha<10°$ or $35°<\alpha<55°$.

11. The method of claim 10, wherein sides of the irregular hexagon are oriented along particular crystal orientations of the sapphire substrate.

12. The method of claim 10, wherein interior angles of the irregular hexagon are between about 90° and 150°.

13. A method of fabricating a nanopore sensor, the method comprising:

depositing a first oxide layer on a first side of a sapphire substrate and a second oxide layer on a second side of the sapphire substrate opposite the first side;

patterning the second oxide layer to form an etch mask having a mask opening in the second oxide layer;

performing a crystalline orientation dependent wet anisotropic etch on the second side of the sapphire substrate using the etch mask to form a cavity having sloped side walls through the sapphire substrate to yield an exposed portion of the first oxide layer, each of the sloped side walls being a crystalline facet aligned with a respective crystalline plane of the sapphire substrate;

depositing a silicon nitride layer on the first oxide layer;

removing the exposed portion of the first oxide layer in the cavity, thereby defining a silicon nitride membrane in the cavity; and forming an opening through the silicon nitride membrane, wherein the opening is a nanopore with a diameter in a range of 1 nm to 20 nm, wherein the mask opening is in the shape of an equilateral triangle, and an edge of the equilateral triangle is aligned at an offset angle $\alpha$ from a crystalline plane of the sapphire substrate, and wherein the silicon nitride membrane is in the shape of an equilateral triangle for $0°<\alpha<20°$ or $40°<\alpha<60°$.

14. The method of claim 13, wherein the etch is conducted at a temperature in a range between 150° C. and 450° C.

15. The method of claim 13, wherein a dimension of a surface of the sapphire substrate is in a range between about 1 mm and about 20 cm and a thickness of the sapphire substrate is in a range between about 0.1 mm and about 1 mm.

* * * * *